US006500652B2

(12) United States Patent
Kao et al.

(10) Patent No.: US 6,500,652 B2

(45) **Date of Patent: *Dec. 31, 2002**

(54) USE OF NUCLEIC ACID MOLECULES AS ANTIVIRAL AGENTS

(75) Inventors: C. Cheng Kao, Berkeley, CA (US); Robert W. Siegel, Los Alamos, NM (US)

(73) Assignee: Advanced Research and Technology Institute, Inc., Indianapolis, IN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/276,192

(22) Filed: Mar. 25, 1999

(65) Prior Publication Data

US 2002/0103143 A1 Aug. 1, 2002

Related U.S. Application Data

(60) Provisional application No. 60/079,459, filed on Mar. 26, 1998.

(51) Int. Cl.[7] .......................... C07H 21/04; C12N 9/00

(52) U.S. Cl. ...................................... 435/183; 536/23.1

(58) Field of Search ......................... 514/44; 536/23.1; 435/235.1, 183; 424/9.1

(56) References Cited

U.S. PATENT DOCUMENTS 5,223,391 A 6/1993 Coen et al.
5,597,697 A 1/1997 Diamond

OTHER PUBLICATIONS

Kandimalla et al., Mixed backbone antisense oligonucleotides: design, biochemical and biological properties of oligonucleotides containing. . . , 1997, Nucleic Acids Research, vol. 25, pp. 370–378.*

Holz et al., 2–Aminopurine as a fluorescent probe for DNA base flipping by methyltransferases, 1998, Nucleic Acids Research, vol. 26, pp. 1076–1083.*

Strobel et al., The 2,6–Diaminopurine riboside.5–Methylisocytidine wobble base pair: An isoenergetic substitution for the study of G.U pairs in RNA, 1994, Biochemistry, vol. 33, 13824–13835.*

Adkins et al. (Jun. 1997) Minimal templates directing accurate initiation of subgenomic RNA synthesis in vitro by the brome mosaic virus RNA–dependent RNA polymerase. RNA 3:634–637.*

Pardigon et al. (Aug. 1993) Multiple binding sites for cellular proteins in the 3' end of the Sindbis alphavirus minus–strand RNA. J. Virol. 67:5003–5011.*

Miller et al. (Feb. 1986) Minus–strand initiation by Brome Mosaic Virus replicase within the 3' tRNA–like structure of native and modified RNA templates. J. Mol. Biol. 187:537–546.*

Rojanasakul (1996) Antisense oligonucleotide therapeutics: drug delivery and targeting. Adv. Drug Del. Rev. 18:115–131.*

Branch (Feb. 1998) A good antisense molecule is hard to find. Trends Biol. Sci. 23:45–50.*

Akhtar et al. (Aug. 1996) Anti–HIV therapy with antisense oligonucleotides and ribozymes: realistic approaches or expnesive myths? J. Antimicrob. Chemother. 38:159–165.*

Kao, C.C., et al., "De Novo Initiation of RNA synthesis by a recombinant flaviridae RNA–dependent RNA polymerase", *Virology, 253*, pp. 1–7, (1999).

Kao, C.C., et al., "Initiation of Minus–Strand RNA Synthesis by the brome mosaic virus RNA–dependent RNA polymerase: Use of oligoribonucleotide primers", *Journal of Virology, 70*(*10*), pp. 6826–6830, (Oct. 1996).

Siegel, R.W., et al., "Sequence–specific recognition of a subgenomic RNA promoter by a viral RNA polymerase", *Proc. Natl. Acad. Sci., 94*, pp. 11238–11243, (Oct. 1997).

Sun, J., et al., "Characterization of RNA Products Associated with or Aborted by a Viral RNA–Dependent RNA Polymerase", *Virology, 236*, pp. 348–353, (1997).

Sun, J., et al., "Initation of (–)–strand RNA synthesis catalyzed by the BMV RNA–dependent RNA polymerase: synthesis of oligonucleotides", *Virology, 226*, pp. 1–12, (1996).

Sun, J., et al., "RNA synthesis by the brome mosaic virus RNA–dependent RNA polymerase: Transition from initiation to elongation", *Virology, 233*, pp. 63–73, (1997).

Adkins, S., et al., "Minimal templates directing accurate initiation of subgenomic RNA synthesis in vitro by the brome mosaic virus RNA–dependent RNA polymerase", *RNA, 3*, Cambridge University Press, 634–647, (1997).

Adkins, S., et al., "Rapid Communication: Subgenomic RNA Promoters Dictate the Mode of Recognition by Bromoviral RNA–Dependent RNA Polymerases", *Virology, 252*, 1–8, (1998).

Huntley, C.C., et al., "Minus sense transcripts of brome mosaic virus RNA–3 Intercistronic region interfere with viral replication", *Virology, 192*, 290–297, (1993).

Siegel, R.W., et al., "Moieties in an RNA Promoter Specifically Recognized by a Viral RNA–dependent RNA Polymerase", *Proc. Nat'l. Acad. Sci. USA*, 11613–11618, (Sep. 1998).

(List continued on next page.)

*Primary Examiner*—Remy Yucel
*Assistant Examiner*—Sita Pappu

(57) ABSTRACT

The invention provides antiviral compounds and compositions comprising a viral specific oligonucleotide. Also provided are methods to inhibit or treat viral infections with the compounds or compositions of the invention.

18 Claims, 16 Drawing Sheets

OTHER PUBLICATIONS

Siegel, R.W., et al., "Sequence–Specific recognition of a subgenomic RNA promoter by a Viral RNA polymerase", *Proc. Natl. Acad. Sci., USA*, vol. 94 , 11238–11243, (Oct. 1997).

Zaccomer, B., et al., "Transgenic plants that express genes including the 3' untranslated region of the turnip yellow mosaic virus (TYMV) genome are partially protected against TYMV infection", *Gene, 136* , 87–94, (1993).

* cited by examiner 1222 1252
3′ CUAGAUACAGGAUUAAGUCGCAUAAUUAUUAGG 5′
−20 +11
| PROSCRIPT | −1+1+2+3+4 | %WT |
|---|---|---|
| WT | GCAUA | 100 +/− 5 |
| −1 G/A | A−−−− | 82 +/− 5 |
| −1 G/U | U−−−− | 100 +/− 11 |
| +2 A/C | −−C−− | 37 +/− 11 |
| +2 A/G | −−G−− | 4 +/− 3 |
| +2 A/U | −−U−− | 66 +/− 6 |
| +3 U/C | −−−C− | 64 +/− 5 |
| +3 U/G | −−−G− | 58 +/− 13 |
| +4 A/C | −−−−C | 92 +/− 8 |
| +4 A/G | −−−−G | 57 +/− 15 |
FIG. 1A
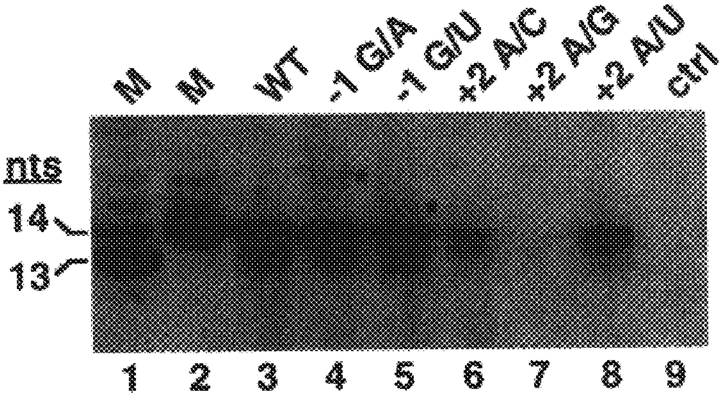
FIG. 1B
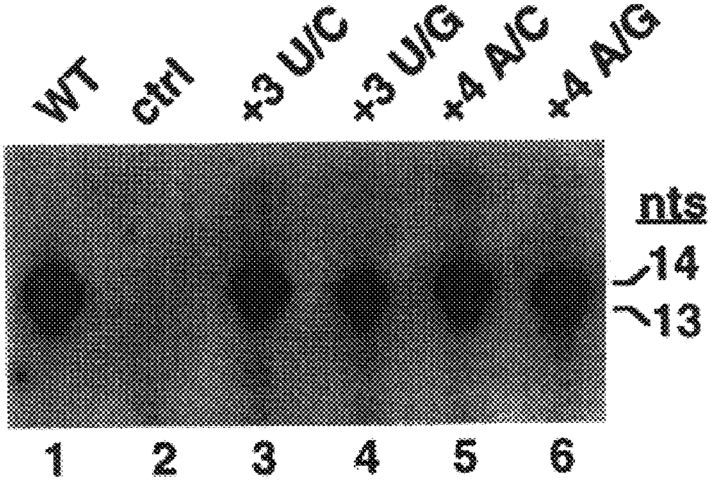
FIG. 1C

PROSCRIPT NAME

THE AMOUNT OF 15 nt PRODUCT SYNTHESIZED FROM THIS TEMPLATE WHICH CONTAINS A WT SUBGENOMIC PROMOTER IS MEASURED IN THE PRESENCE OF INCREASING AMOUNTS OF THE DNA INHIBITORS LISTED BELOW.

| | $I_{50}$ (μM) | |
|---|---|---|
| −1/13 dU (CONTAINS DEOXYURIDUNES) | 0.125 | 3' d (GCAUAAUUAUCAGG) 5' |
| −1/8 dU (CONTAINS DEOXYURIDUNES) | 4.2 | 3' d (GCAUAAUGG) 5' |
| −1/8 dT (THYMINES REPLACE URIDINES) | 2.5 | 3' d (GCATAATGG) 5' |

SEQUENCES:

H1 3' cu aga uac agg auu aag ucg caU AAU UAU UAG G 5'
H2 3' cu aga uac agg auu aag ucg CAU AAU UAU UAG G 5'
H3 3' CU AgA Uac AgG AUU AAG UCG caU AAU DAU UAG G 5'
H4 3' cu aga uac agg auu aag ucg caT AAT TAT TAG G 5'

FIG. 11

| NAME | | −20 | % ACTIVITY |
|---|---|---|---|
| WT | 3' | CUAGAUACAGGAUUAAGUCGCAUAAUUAUUAGG | 100 |
| H1 | | CUAGAUACAGGAUUAAGUCGCAuaauuauuagg | 20 |
| H4 | | CUAGAUACAGGAUUAAGUCGCAtaattattagg | 17 |
| H2 | | CUAGAUACAGGAUUAAGUCGcauaauuauuagg | 19 |
| H3 | | cuaGauACaGgauuaagucgCAuaauuauuagg | 32 |
| dWT | 3' | cuagauacaggauuaagucgcauaauuauuagg | 6 |
| −11g/2' | H | CUAGAUACAgGAUUAAGUCGCAUAAUUAUUAGG | 46 |

FIG. 12

SEQUENCE LISTING

<160> NUMBER OF SEQ ID NOS: 36

<210> SEQ ID NO 1
<211> LENGTH: 33
<212> TYPE: RNA
<213> ORGANISM: Brome mosaic virus
<220> FEATURE:
<221> NAME/KEY: misc_RNA
<222> LOCATION: (1)...(2)
<223> OTHER INFORMATION: Two additional guanylates

<400> SEQUENCE: 1
ggauuauuaa uacgcugaau uaggacauag auc 33

<210> SEQ ID NO 2
<211> LENGTH: 33
<212> TYPE: RNA
<213> ORGANISM: Artificial Sequence
<220> FEATURE:
<223> OTHER INFORMATION: This is an artificial sequence having nucleotide substitutions relative to the wild-type 33 nucleotide sequence encompassing the (-)-strand complement of nucleotides 1222-1252 of RNA3
<221> NAME/KEY: misc_RNA
<222> LOCATION: (1)...(2)
<223> OTHER INFORMATION: Two additional guanylates

<400> SEQUENCE: 2
ggauuauuaa uacacugaau uaggacauag auc 33

<210> SEQ ID NO 3
<211> LENGTH: 33
<212> TYPE: RNA
<213> ORGANISM: Artificial Sequence
<220> FEATURE:
<223> OTHER INFORMATION: This is an artificial sequence having nucleotide substitutions relative to the wild-type 33 nucleotide sequence encompassing the (-)-strand complement of nucleotides 1222-1252 of RNA3
<221> NAME/KEY: misc_RNA
<222> LOCATION: (1)...(2)
<223> OTHER INFORMATION: Two additional guanylates

<400> SEQUENCE: 3
ggauuauuaa uacucugaau uaggacauag auc 33

<210> SEQ ID NO 4
<211> LENGTH: 33
<212> TYPE: RNA
<213> ORGANISM: Artificial Sequence
<220> FEATURE:
<223> OTHER INFORMATION: This is an artificial sequence having nucleotide substitutions relative to the wild-type 33 nucleotide sequence encompassing the (-)-strand complement of nucleotides 1222-1252 of RNA3
<221> NAME/KEY: misc_RNA
<222> LOCATION: (1)...(2)
<223> OTHER INFORMATION: Two additional guanylates

<400> SEQUENCE: 4
ggauuauuaa uccgcugaau uaggacauag auc 33

<210> SEQ ID NO 5
<211> LENGTH: 33
<212> TYPE: RNA
<213> ORGANISM: Artificial Sequence
<220> FEATURE:
<223> OTHER INFORMATION: This is an artificial sequence having -continued

```
      nucleotide substitutions relative to the wild-type 33
      nucleotide sequence encompassing the (-)-strand
      complement of nucleotides 1222-1252 of RNA3
<221> NAME/KEY: misc_RNA
<222> LOCATION: (1)...(2)
<223> OTHER INFORMATION: Two additional guanylates

<400> SEQUENCE: 5

ggauuauuaa ugcgcugaau uaggacauag auc                                33


<210> SEQ ID NO 6
<211> LENGTH: 33
<212> TYPE: RNA
<213> ORGANISM: Artificial Sequence
<220> FEATURE:
<223> OTHER INFORMATION: This is an artificial sequence having
      nucleotide substitutions relative to the wild-type 33
      nucleotide sequence encompassing the (-)-strand
      complement of nucleotides 1222-1252 of RNA3
<221> NAME/KEY: misc_RNA
<222> LOCATION: (1)...(2)
<223> OTHER INFORMATION: Two additional guanylates

<400> SEQUENCE: 6

ggauuauuaa uucgcugaau uaggacauag auc                                33


<210> SEQ ID NO 7
<211> LENGTH: 33
<212> TYPE: RNA
<213> ORGANISM: Artificial Sequence
<220> FEATURE:
<223> OTHER INFORMATION: This is an artificial sequence having
      nucleotide substitutions relative to the wild-type 33
      nucleotide sequence encompassing the (-)-strand
      complement of nucleotides 1222-1252 of RNA3
<221> NAME/KEY: misc_RNA
<222> LOCATION: (1)...(2)
<223> OTHER INFORMATION: Two additional guanylates

<400> SEQUENCE: 7

ggauuauuaa cacgcugaau uaggacauag auc                                33


<210> SEQ ID NO 8
<211> LENGTH: 33
<212> TYPE: RNA
<213> ORGANISM: Artificial Sequence
<220> FEATURE:
<223> OTHER INFORMATION: This is an artificial sequence having
      nucleotide substitutions relative to the wild-type 33
      nucleotide sequence encompassing the (-)-strand
      complement of nucleotides 1222-1252 of RNA3
<221> NAME/KEY: misc_RNA
<222> LOCATION: (1)...(2)
<223> OTHER INFORMATION: Two additional guanylates

<400> SEQUENCE: 8

ggauuauuaa gacgcugaau uaggacauag auc                                33


<210> SEQ ID NO 9
<211> LENGTH: 33
<212> TYPE: RNA
<213> ORGANISM: Artificial Sequence
<220> FEATURE:
<223> OTHER INFORMATION: This is an artificial sequence having
      nucleotide substitutions relative to the wild-type 33
      nucleotide sequence encompassing the (-)-strand
      complement of nucleotides 1222-1252 of RNA3
<221> NAME/KEY: misc_RNA
<222> LOCATION: (1)...(2)
<223> OTHER INFORMATION: Two additional guanylates
```

-continued

<400> SEQUENCE: 9
ggauuauuac uacgcugaau uaggacauag auc 33

<210> SEQ ID NO 10
<211> LENGTH: 33
<212> TYPE: RNA
<213> ORGANISM: Artificial Sequence
<220> FEATURE:
<223> OTHER INFORMATION: This is an artificial sequence having nucleotide substitutions relative to the wild-type 33 nucleotide sequence encompassing the (-)-strand complement of nucleotides 1222-1252 of RNA3
<221> NAME/KEY: misc_RNA
<222> LOCATION: (1)...(2)
<223> OTHER INFORMATION: Two additional guanylates

<400> SEQUENCE: 10
ggauuauuag uacgcugaau uaggacauag auc 33

<210> SEQ ID NO 11
<211> LENGTH: 31
<212> TYPE: RNA
<213> ORGANISM: Semliki forest virus

<400> SEQUENCE: 11
ggcgcaccaa uuuaggaccg ccguagaggu g 31

<210> SEQ ID NO 12
<211> LENGTH: 22
<212> TYPE: RNA
<213> ORGANISM: Semliki forest virus

<400> SEQUENCE: 12
auuuaggacc gccguagagg ug 22

<210> SEQ ID NO 13
<211> LENGTH: 22
<212> TYPE: RNA
<213> ORGANISM: Ross river virus

<400> SEQUENCE: 13
auuuaggacc gccguagagg ug 22

<210> SEQ ID NO 14
<211> LENGTH: 22
<212> TYPE: RNA
<213> ORGANISM: Middelburg virus

<400> SEQUENCE: 14
auuuaggacc gccguagagg uc 22

<210> SEQ ID NO 15
<211> LENGTH: 22
<212> TYPE: RNA
<213> ORGANISM: Sinbis virus

<400> SEQUENCE: 15
auuuaggacc accguagaga ug 22

<210> SEQ ID NO 16
<211> LENGTH: 23
<212> TYPE: RNA
<213> ORGANISM: Cucumber mosaic virus

<400> SEQUENCE: 16

-continued acgcaaucuc gcggagaagc auc 23

<210> SEQ ID NO 17
<211> LENGTH: 24
<212> TYPE: RNA
<213> ORGANISM: Alfalfa mosaic virus

<400> SEQUENCE: 17
acggcccauu accgaucaau gauc 24

<210> SEQ ID NO 18
<211> LENGTH: 27
<212> TYPE: RNA
<213> ORGANISM: Broad bean mottle virus

<400> SEQUENCE: 18
augcguaaca cggucggaga cugcaac 27

<210> SEQ ID NO 19
<211> LENGTH: 22
<212> TYPE: RNA
<213> ORGANISM: Cowpea chlorotic mottle virus

<400> SEQUENCE: 19
acuaucaaau uaaacauaga uu 22

<210> SEQ ID NO 20
<211> LENGTH: 22
<212> TYPE: RNA
<213> ORGANISM: Brome mosaic virus

<400> SEQUENCE: 20
acgcugaauu aggacauaga uc 22

<210> SEQ ID NO 21
<211> LENGTH: 17
<212> TYPE: RNA
<213> ORGANISM: Brome mosaic virus

<400> SEQUENCE: 21
gucgacauua uuaauac 17

<210> SEQ ID NO 22
<211> LENGTH: 14
<212> TYPE: DNA
<213> ORGANISM: Artificial Sequence
<220> FEATURE:
<223> OTHER INFORMATION: A DNA inhibitor

<400> SEQUENCE: 22
ggacuauuaa uacg 14

<210> SEQ ID NO 23
<211> LENGTH: 9
<212> TYPE: DNA
<213> ORGANISM: Artificial Sequence
<220> FEATURE:
<223> OTHER INFORMATION: A DNA inhibitor

<400> SEQUENCE: 23 gguaauacg 9

<210> SEQ ID NO 24

-continued

<211> LENGTH: 9
<212> TYPE: DNA
<213> ORGANISM: Artificial Sequence
<220> FEATURE:
<223> OTHER INFORMATION: A DNA inhibitor

<400> SEQUENCE: 24 ggtaatacg 9

<210> SEQ ID NO 25
<211> LENGTH: 33
<212> TYPE: DNA
<213> ORGANISM: Brome mosaic virus
<220> FEATURE:
<221> NAME/KEY: misc_feature
<222> LOCATION: (12)...(33)
<223> OTHER INFORMATION: This is a mixed RNA/DNA sequence with RNA at positions 12-33.
<221> NAME/KEY: misc_feature
<222> LOCATION: (1)...(2)
<223> OTHER INFORMATION: Two additional guanylates

<400> SEQUENCE: 25
ggauuauuaa uacgcugaau uaggacauag auc 33

<210> SEQ ID NO 26
<211> LENGTH: 33
<212> TYPE: DNA
<213> ORGANISM: Brome mosaic virus
<220> FEATURE:
<221> NAME/KEY: misc_feature
<222> LOCATION: (14)...(33)
<223> OTHER INFORMATION: This is a mixed RNA/DNA sequence with RNA at positions 14-33.
<221> NAME/KEY: misc_feature
<222> LOCATION: (1)...(2)
<223> OTHER INFORMATION: Two additional guanylates

<400> SEQUENCE: 26
ggauuauuaa uacgcugaau uaggacauag auc 33

<210> SEQ ID NO 27
<211> LENGTH: 33
<212> TYPE: DNA
<213> ORGANISM: Brome mosaic virus
<220> FEATURE:
<221> NAME/KEY: misc_feature
<222> LOCATION: 12, 13, 24, 26, 27, 30
<223> OTHER INFORMATION: This is a mixed RNA/DNA sequence with RNA at positions 12, 13, 24, 26, 27 and 30
<221> NAME/KEY: misc_feature
<222> LOCATION: (1)...(2)
<223> OTHER INFORMATION: Two additional guanylates

<400> SEQUENCE: 27
ggauuaduaa uacgcugaau uaggacauag auc 33

<210> SEQ ID NO 28
<211> LENGTH: 33
<212> TYPE: DNA
<213> ORGANISM: Brome mosaic virus
<220> FEATURE:
<221> NAME/KEY: misc_feature
<222> LOCATION: (12)...(33)
<223> OTHER INFORMATION: This is a mixed RNA/DNA sequence with RNA at positions 12-33.
<221> NAME/KEY: misc_feature
<222> LOCATION: (1)...(2)
<223> OTHER INFORMATION: Two additional guanylates

<400> SEQUENCE: 28

-continued ggattattaa tacgcugaau uaggacauag auc 33

<210> SEQ ID NO 29
<211> LENGTH: 33
<212> TYPE: RNA
<213> ORGANISM: Brome mosaic virus
<220> FEATURE:
<221> NAME/KEY: misc_RNA
<222> LOCATION: (1)...(2)
<223> OTHER INFORMATION: Two additional guanylates

<400> SEQUENCE: 29
ggauuauuaa uacgcugaau uaggacauag auc 33

<210> SEQ ID NO 30
<211> LENGTH: 33
<212> TYPE: DNA
<213> ORGANISM: Brome mosaic virus
<220> FEATURE:
<221> NAME/KEY: misc_feature
<222> LOCATION: (12)...(33)
<223> OTHER INFORMATION: This is a mixed RNA/DNA sequence with RNA at positions 12-33.
<221> NAME/KEY: misc_feature
<222> LOCATION: (1)...(2)
<223> OTHER INFORMATION: Two additional guanylates

<400> SEQUENCE: 30
ggauuauuaa uacgcugaau uaggacauag auc 33

<210> SEQ ID NO 31
<211> LENGTH: 33
<212> TYPE: DNA
<213> ORGANISM: Brome mosaic virus
<220> FEATURE:
<221> NAME/KEY: misc_feature
<222> LOCATION: (12)...(33)
<223> OTHER INFORMATION: This is a mixed RNA/DNA sequence with RNA at positions 12-33.
<221> NAME/KEY: misc_feature
<222> LOCATION: (1)...(2)
<223> OTHER INFORMATION: Two additional guanylates

<400> SEQUENCE: 31
ggattattaa tacgcugaau uaggacauag auc 33

<210> SEQ ID NO 32
<211> LENGTH: 33
<212> TYPE: DNA
<213> ORGANISM: Brome mosaic virus
<220> FEATURE:
<221> NAME/KEY: misc_feature
<222> LOCATION: (14)...(33)
<223> OTHER INFORMATION: This is a mixed RNA/DNA sequence with RNA at positions 14-33.
<221> NAME/KEY: misc_feature
<222> LOCATION: (1)...(2)
<223> OTHER INFORMATION: Two additional guanylates

<400> SEQUENCE: 32
ggauuauuaa uacgcugaau uaggacauag auc 33

<210> SEQ ID NO 33
<211> LENGTH: 33
<212> TYPE: DNA
<213> ORGANISM: Brome mosaic virus
<220> FEATURE:
<221> NAME/KEY: misc_feature
<222> LOCATION: 12, 13, 24, 26, 27, 30

-continued

```
<223> OTHER INFORMATION: This is a mixed RNA/DNA sequence with RNA at
      positions 12, 13, 24, 26, 27 and 30
<221> NAME/KEY: misc_feature
<222> LOCATION: (1)...(2)
<223> OTHER INFORMATION: Two additional guanylates

<400> SEQUENCE: 33

ggauuauuaa uacgcugaau uaggacauag auc                                33


<210> SEQ ID NO 34
<211> LENGTH: 33
<212> TYPE: DNA
<213> ORGANISM: Brome mosaic virus
<220> FEATURE:
<221> NAME/KEY: misc_feature
<222> LOCATION: (1)...(2)
<223> OTHER INFORMATION: Two additional guanylates

<400> SEQUENCE: 34

ggauuauuaa uacgcugaau uaggacauag auc                                33


<210> SEQ ID NO 35
<211> LENGTH: 33
<212> TYPE: DNA
<213> ORGANISM: Brome mosaic virus
<220> FEATURE:
<221> NAME/KEY: misc_feature
<222> LOCATION: 1-23, 25-33
<223> OTHER INFORMATION: This is a mixed RNA/DNA sequence with RNA at
      positions 1-23 and 25-33.
<221> NAME/KEY: misc_feature
<222> LOCATION: (1)...(2)
<223> OTHER INFORMATION: Two additional guanylates

<400> SEQUENCE: 35

ggauuauuaa uacgcugaau uaggacauag auc                                33


<210> SEQ ID NO 36
<211> LENGTH: 21
<212> TYPE: RNA
<213> ORGANISM: Brome mosaic virus

<400> SEQUENCE: 36

cgcugaauua ggacauagau c                                             21
```

USE OF NUCLEIC ACID MOLECULES AS ANTIVIRAL AGENTS

CROSS-REFERENCE TO RELATED APPLICATION

This application claims the benefit of, U.S. application Ser. No. 60/079,459, filed Mar. 26, 1998, the disclosure of which is incorporated by reference herein.

STATEMENT OF GOVERNMENT RIGHTS

The invention was made with a grant from the Government of the United States of America (Grant # MCB950-7344 from the National Science Foundation and Grant #9702126 from the United States Department of Agriculture). The Government may have certain rights in the invention.

BACKGROUND OF THE INVENTION

Viral RNA replication, a process fundamental to viral pathogenicity, requires specific recognition of RNA features by proteins. RNA-dependent RNA polymerase (RdRp) is a complex composed of viral and cellular proteins that directs viral RNA synthesis from infecting RNA templates. Many viral RdRp proteins have been sequenced and analyzed. However, a comprehensive mechanism describing RNA synthesis is lacking. Consequently, general knowledge of RdRp is significantly less than that of other RNA and DNA polymerases.

Viruses are obligate parasites which depend upon the infected host for many of the basic processes needed for a successful infection. Because viruses depend on the enzymatic and synthetic functions of the host cell, it is very difficult to treat viral infections without affecting cellular processes. For example, interferon causes significant and widespread changes in the cell and hence leads to a number of side effects, including fever, nausea, and other discomforts. Given that several viral diseases are at pandemic proportions, including influenza, AIDS, and hepatitis, the design of effective virus-specific drugs is increasingly important.

Potential antiviral drugs are usually subjected to an intensive and costly screening program to determine whether the drug can preferentially inhibit a viral process. One such drug is Aziduovir, which is utilized more readily by the reverse transcriptase of the human immunodeficiency virus (HIV) than by host cellular polymerases. Yet other potential antiviral therapies, including antisense molecules and ribozymes, are difficult to produce due to the need for complex molecular recombinant technology.

Thus, there is a continuing need for agents that specifically inhibit viral replication.

SUMMARY OF THE INVENTION

The invention provides an isolated and purified nucleic acid sequence that can be used as a specific inhibitor of viral RNA synthesis, i.e., an inhibitor of the viral polymerase. In particular, the present invention provides an isolated and purified oligonucleotide of at least four nucleotides, wherein the oligonucleotide comprises a viral nucleic acid sequence which includes the viral initiation nucleotide. Preferably, the oligonucleotide includes viral initiation sequences and optionally viral promoter sequences.

As described hereinbelow, the sequences needed for the replication of a (+) single strand RNA virus, brome mosaic virus (BMV), have been determined. These sequences are needed to correctly and efficiently initiate RNA synthesis. Mutations in the promoter or initiation sequences of BMV abolish RNA synthesis by the BMV RNA-dependent RNA polymerase (RdRp). Moreover, as the promoter and initiation sequences are conserved in several RNA viruses, the mechanism of RNA synthesis is likely to be very similar in all RNA viruses with genomes of (+)-sense RNA. Furthermore, mutations in the initiation sequences will not result in a decrease in the efficacy of the nucleic acid sequences of the invention, as these mutations result in a decrease in viral replication.

The oligonucleotide preferably includes the initiation nucleotide and at least the first, and more preferably the first two nucleotides which are 3' of the initiation nucleotide in the viral sequence. An oligonucleotide of the invention, or a plurality thereof, is useful to prepare an antiviral composition. The antiviral compositions of the invention are particularly useful in methods to inhibit the infection or replication of (+) single strand RNA viruses, such as the alpha virus superfamily, which includes bacterial, plant and animal viruses. The oligonucleotide of the invention may comprise DNA or RNA, or a hybrid thereof. Preferably, the oligonucleotide is DNA. It is also preferred that the oligonucleotide of the invention comprises at least about four to about fifty, more preferably at least about eight to about forty, even more preferably at least about twenty to about thirty-five, and yet even more preferably at least about eight to about thirteen, contiguous nucleotide bases that preferably have at least about 90%, more preferably at least about 95%, and even more preferably 100%, contiguous nucleotide sequence identity to a particular wild-type viral sequence. However, the invention is not limited to oligonucleotides having identity to a wild type viral promoter and/or initiation sequence, as nucleotides may be substituted with analogs thereof, e.g., analogs of nucleotide bases. Preferred nucleotide analogs are those which have enhanced adsorption for human cells and/or enhanced stability in human serum relative to native nucleotides. For example, the incorporation of sulfur residues in an oligonucleotide, e.g., in the RNA backbone, increases the binding of RdRp to the oligonucleotide. Oligonucleotides may be prepared by methods well known to the art.

Also provided is a method to inhibit or treat a viral infection which employs at least one oligonucleotide of the invention. The method comprises the administration to a cell having, or suspected of having, a viral infection, an effective amount of at least one oligonucleotide of the invention, wherein the oligonucleotide comprises the initiation nucleotide for the virus. For example, as shown in FIG. 7, a DNA oligonucleotide of the invention inhibits viral RNA replication in vitro at a concentration in the micromolar range. The DNA oligonucleotides of the invention may be modified in such a manner so as to prevent RdRp release, e.g., by the incorporation of abasic residues, bulky blocking groups, terminal nucleotides with aliphatic moieties, or covalent crosslinker.

The present invention may be superior to other known antiviral agents because it requires only the nucleic acid sequence(s) for initiation of viral nucleic acid synthesis. Thus, the sequence is readily prepared, does not require complex manipulation by molecular biology techniques, and only a minimal screening regime is necessary. Moreover, the present oligonucleotides may be modified to increase their efficacy at lower concentrations, e.g., RNA oligonucleotides may be modified so as to contain nucleotide analogs or be subjected to circularization, to provide agents that are more stable in vivo so as to, for example, have increased resistance to degradation in serum. Given that every virus will have a minimum of one, and more likely at least two, sequences needed for the initiation of nucleic acid synthesis, at least one, preferably two, and more preferably three (for viruses with subgenomic promoters), therapeutics can be designed for every virus. In particular, a nucleic acid sequence can be prepared to inhibit genomic as well as subgenomic (internal initiation from subgenomic promoters) nucleic acid synthesis. In addition, a particular inhibitor may also be used to disrupt other steps in viral replication, e.g., translation, protein and nucleic acid modification, which may be tightly linked to the initiation of RNA synthesis. Thus, an oligonucleotide of the invention may be employed in combination with other anti-viral agents.

As used herein, the terms "isolated and/or purified" refer to in vitro preparation, isolation and/or purification of an oligonucleotide of the invention, so that it is not associated with in vivo substances.

BRIEF DESCRIPTION OF THE FIGURES

FIG. 1. (A) Complete sequence of the wild-type (WT) 33 nt proscript (SEQ ID NO:1) encompassing the (−)-strand complement of nts 1222–1252 of RNA3 representing nts −20 to +11 relative to the initiation site (indicated with arrow) for subgenomic RNA synthesis. Two additional guanylates incorporated by T7 DdRp are shown at the 5' end of the prescript. The initiation sequence (−1 to +4) is expanded below the WT proscript. Proscripts are named for the mutation shown in the sequence (SEQ ID NOs:2–10). WT nucleotides are represented with a dash. Relative amounts of RdRp products normalized to WT following quantitation with a phosphorimager are presented to the right of the sequence. Values represent the mean and standard deviation from four independent experiments.

FIG. 1 (B) Autoradiograph of RdRp products synthesized from proscripts containing mutations at −1 or +2 nts of template for subgenomic synthesis and analyzed by electrophoresis on a 20% denaturing polyacrylamide gel. Lanes 1 and 2 contain 13 and 14 nt RNAs synthesized by T7 DdRp. Bands of higher molecular weight represent products of reiterative transcription by T7 DdRp. Proscripts used in reactions (lanes 3–8) and a control (ctrl) reaction to which no template was added (lane 9) are noted above the autoradiograph. Relative sizes of the T7 markers (in nts) are indicated at the left of the autoradiograph. RdRp products initiated from alternative sites are indicated with an asterisk (*) to the right of their position.

FIG. 1 (C) Autoradiograph of RdRp products synthesized from proscripts containing mutations at +3 and +4 nts of template for subgenomic RNA synthesis. Proscripts used in reactions (lanes 1 and 3–6) and a control (ctrl) reaction to which no template was added (lane 2) are noted above the autoradiograph.

FIG. 4 (B) Predominant oligonucleotides synthesized from proscript 12/26 are 6, 7 and 9 nt in size. Autoradiograph of RdRp products synthesized from proscript 12/26 and analyzed by electrophoresis on a 24% denaturing polyacrylamide gel. The molecular weight markers used in this experiment were generated by T7 DdRp and are of the expected sequence of 8 and 13 nt RNAs correctly initiated by the BMV RdRp. Lanes 1 and 2 contain the 8 nt marker (and smaller T7 DdRp-generated abortive and larger T7 DdRp-generated reiterative products) with twice the amount being loaded in lane 1. Lane 6 contains the 13 nt marker and smaller T7 DdRp-generated abortive and larger T7 DdRp-generated reiterative products. Lanes 3–5 contain the products from RdRp reactions containing proscript 12/26 as template. The positions (in nts) of the size markers and T7 abortive products are indicated to the left of the autoradiograph. The positions of the full-length 26 nt product, a prematurely terminated 24 nt product and the 6, 7 and 9 nt oligonucleotides synthesized by RdRp are indicated to the right of the autoradiograph.

FIG. 4 (C) Oligonucleotides are accurately initiated from the subgenomic promoter. Template and radiolabel ([α-$^{32}$P]ATP or [α-$^{32}$P]CTP) included in and NTPs omitted from reactions are indicated above the autoradiograph of the 24% denaturing polyacrylamide gel. The lengths (in nts) of full-length and oligonucleotide products are indicated to the left of the autoradiograph.

FIG. 4 (D) Effect of unlabeled ATP on synthesis of subgenomic and oligonucleotide RNAs from full-length (−)-strand RNA3. Autoradiograph of RdRp reaction products analyzed by electrophoresis on a 20% denaturing polyacrylamide gel with 5% stacking gel. Unlabeled ATP was included in reactions at final concentrations of 0, 1, 2, 5, 10 or 30 μM in lanes 1–6. Lane 7 contains the 13 nt marker and an unexplained higher molecular weight band. The lengths (in nts) of subgenomic, marker and oligonucleotide RNAs are indicated to the left of the autoradiograph. FIG. 4 (E) Effect of $MnCl_2$ on synthesis of subgenomic and oligonucleotide RNAs from full-length (−)-strand RNA3. Autoradiograph of RdRp reaction products analyzed by electrophoresis on a 10% denaturing polyacrylamide gel with 5% stacking gel. $MnCl_2$ was included in reactions at final concentrations of 0, 1, 2, 5, 10 or 20 mM in lanes 1–6. Lane 7 contains the products form a control reaction (ctrl) to which no template was added. The lengths (in nts) of subgenomic and oligonucleotide RNAs are indicated to the left of the autoradiograph. A novel oligonucleotide induced by $MnCl_2$ is noted with an arrow to the right of the autoradiograph.

FIG. 5 (B) Location of elongated RNAs and oligonucleotides following spin column fractionation of the initial reaction. Fractions were phenol:chloroform extracted and ethanol precipitated (with 10 $\mu$g glycogen) prior to analysis on a 24% denaturing polyacrylamide gel followed by autoradiography. Fraction numbers are indicated at the top of the autoradiograph and the positions of elongated RNAs and oligonucleotides are shown at the left.

FIG. 5 (C) Location of RdRp activity following spin column fractionation of the initial reaction. Fractions were tested for RdRp activity using BMV virion RNA (vRNA) as template in standard RdRp assays. RdRp products were analyzed by electrophoresis on a 1% agarose gel followed by autoradiography. Fraction numbers are indicated at the top of the autoradiograph and the positions of vRNA products are shown at the left.

FIG. 6 (B) Termination of subgenomic RNA synthesis. Autoradiograph of RdRp products synthesized from the indicated templates and separated by 1% agarose gel electrophoresis. The positions of RdRp products from BMV virion RNA (vRNA) (lane 1) are shown at the left of the autoradiograph. The products of a control reaction (ctrl) containing no added template are shown in lane 4. The position of the subgenomic RNA with the 250 nt extension is indicated with an arrow at the right of the autoradiograph. FIG. 6 (C) Termination of genomic (−)-strand RNA3 synthesis. Autoradiograph of RdRp products synthesized from the indicated templates and separated by 1% agarose gel electrophoresis. The position of the RNA3 with the 150 nt extension is indicated with an arrow at the right of the autoradiograph. The autoradiograph of lanes 2–4 was exposed four times longer than the autoradiograph of lane 1.

FIG. 9 (B) The BMV RdRp can utilize the promoter from BMV and SFV. Lane 1: Molecular marker of the same size as the RdRp product synthesized from the BMV promoter. The SFV promoter is designed to generate an 11 nt product (lanes 2–4). The right-most lane was performed with no exogenous templates. Amounts and identity of the templates used in each reaction is shown above the autoradiograph.

FIG. 11. Hybrid oligonucleotides. Sequence in lower case indicate ribonucleotides while upper case indicate deoxyribonucleotides. U in capital letters indicates deoxyuridines. These hybrids, like their wild type RNA or DNA counterparts, are likely able to inhibit viral replication.

FIG. 12. Activity of hybrid oligonucleotides.

DETAILED DESCRIPTION OF THE INVENTION

Figure 2:
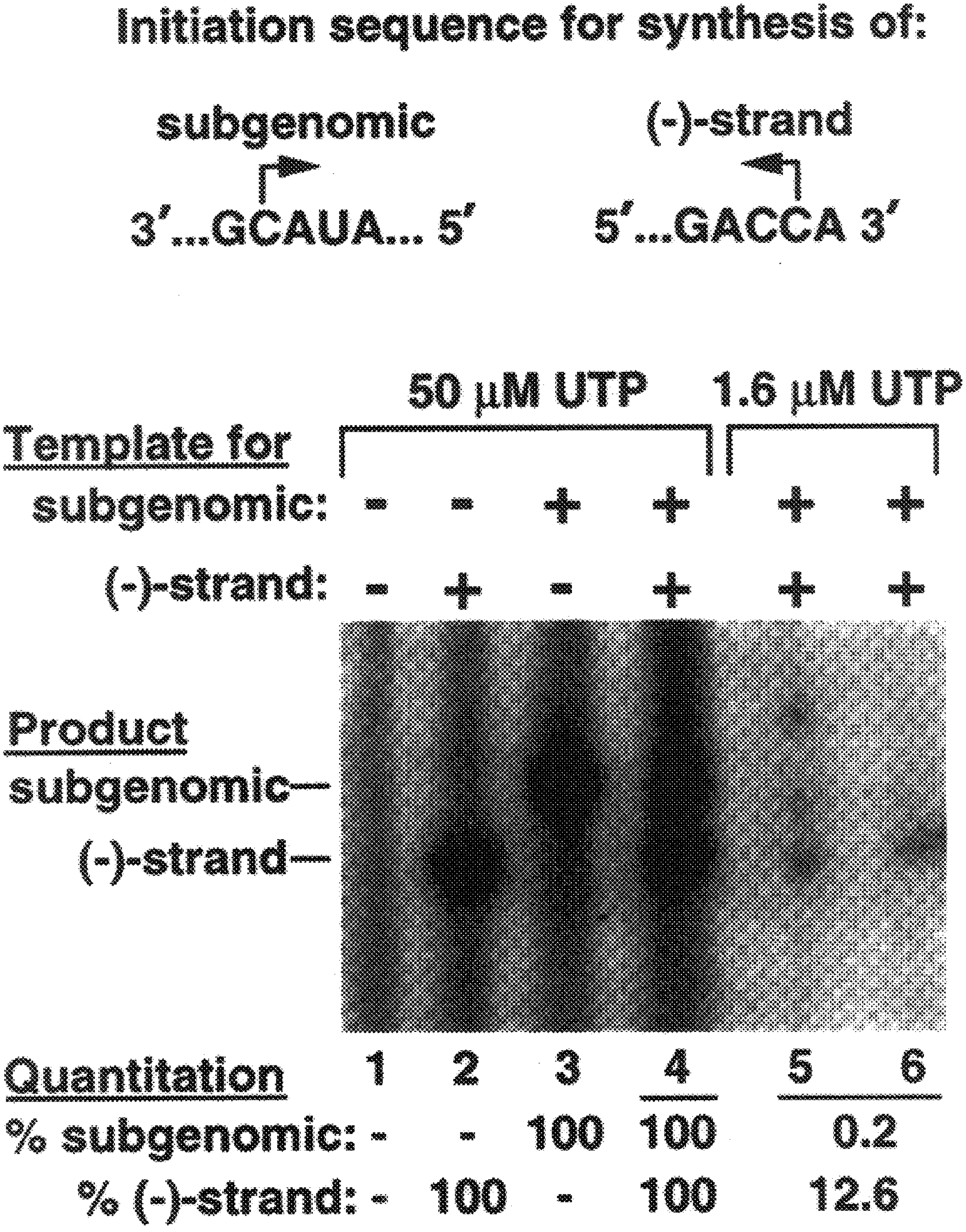
FIG. 2. UTP concentration requirement for synthesis of subgenomic and (−)-strand RNA in vitro. Sequences surrounding the initiation sites (indicated with arrows) in templates for subgenomic (up/45; directing synthesis of a 207 nt subgenomic RNA) and (−)-strand (B3-198; directing synthesis of a 198 nt (−)-strand RNA3) synthesis are shown. RdRp products from these templates were treated with S1 nuclease and then analyzed by electrophoresis on a 5% denaturing polyacrylamide gel followed by autoradiography. Templates and UTP concentrations used in RdRp reactions are indicated above the autoradiograph. Positions of the subgenomic and (−)-strand products are indicated to the left of the autoradiograph. Relative amounts of RdRp products normalized to those synthesized at 50 μM UTP are shown below the autoradiograph.

As the structures of several different polymerases appear conserved, it has been suggested that the mechanism of nucleic acid synthesis is also conserved. The best characterized polymerases are the DNA-dependent RNA polymerases (DdRp) that are responsible for transcription. DNA-dependent RNA synthesis has been divided into a number of biochemically distinct steps: binding of the DdRp to the promoter, formation of a transcriptionally active open complex, synthesis of the first phosphodiester bond, abortive RNA synthesis, promoter clearance, processive elongation and termination. The progression of these steps is accompanied by increases in the affinity of the interaction between the polymerase and the template, with commitment of the polymerase to the template taking place during/soon after the first translocation step. The committed polymerase is thought to remain stably associated with the template even though additional nucleotides needed for elongation may be lacking in the reaction).

Viral RNA replication is mediated by RNA-dependent RNA polymerases (RdRp). For a positive-sense RNA virus, the genomic (+)-strand RNA serves as a template for synthesis of (−)-strand RNA which, in turn, serves as a template for synthesis of additional copies of genomic (+)-strand RNA and, in many viruses, (+)-strand subgenomic RNAs.

Elucidating the details of RNA synthesis by RdRp may provide the foundation for studies of RNA repair and recombination and allow a comparison to RNA synthesis by DdRp. Results from previous characterization of in vitro RNA synthesis by the BMV RdRp defined several steps, including: (1) initiation of RNA synthesis at the penultimate cytidylate at the 3' end of BMV (+)-strand templates (Miller et al., 1985; Kao and Sun, 1996), (2) abortive oligoribonucleotide synthesis (Sun et al., 1996), and (3) processive RNA synthesis (Sun and Kao, 1997). Steps in RNA synthesis by RdRp appear to mirror those seen in transcription by DdRps, including the release of abortive initiation products and the progression to elongation after the synthesis of nascent RNAs of 8 to 10 nt. This is perhaps not surprising since the catalytic subunits of all polymerases share common structural and functional motifs.

Despite the overall similarities in RNA synthesis by DdRps and RdRp, several differences should be mentioned. First, RdRp usually initiates RNA synthesis from the ends of RNA templates rather than exclusively from a promoter within a DNA molecule as does DdRp (Miller et al., 1986; Ishihama and Nagata, 1988; Kao and Sun, 1996). Second, RdRp appears to dissociate from the template during the abortive initiation step (Sun and Kao, 1997), whereas the T7 RNA polymerase remains more stably bound to supercoiled DNA, although the stability of the T7 RNA polymerase-DNA interaction is highly dependent on the structure of the template (Diaz et al., 1996). Third, stability of the DdRp ternary complex is maintained primarily by RNA-protein and DNA-protein interactions, and not by RNA-DNA interactions (Altmann et al., 1994). For RdRp, it is possible that for some viruses, an intermediate of (−)-strand RNA synthesis is a double-stranded hybrid composed of the nascent and template RNAs (Baltimore, 1968; Takeda et al., 1986; Bienz et al., 1992; de Graaff et al., 1995). If true, then the duplex may contribute to the stability of RdRp ternary complex.

Brome mosaic virus (BMV) is a useful model to define the steps in RNA synthesis for (+)-strand RNA virus. BMV has three genomic RNAs, designated RNA1, 2, and 3 and a subgenomic RNA4. These RNAs encode four proteins: the helicase-like 1a (109 kDA), the polymerase-like 2a (96 kDa), the movement protein 3a (34 kDa), and the capsid protein (20 kDa). Each BMV RNA contains a highly conserved 3' region which folds into a tRNA-like structure that is required to direct the synthesis of (−)-strand RNA. The (−)-strand RNA serves as template and provides cis-acting sequences for genomic (+)-strand and subgenomic RNA synthesis.

The BMV RNA replication enzyme is a complex localized in the endoplasmic reticulum. It contains the BMV-encoded 1a and 2a proteins and yet unidentified host proteins. Membrane-associated replicase can be solubilized with nonionic detergents and still retain the ability to direct synthesis of (−)-strand RNAs or subgenomic (+)-strand RNA from exogenously added genomic RNAs or (−)-strand BMV RNA3, respectively. Detergent-solubilized BMV replicase, named RNA-dependent RNA polymerase (RdRp), can utilize (+)-strand RNAs of less than 160 nucleotides containing the conserved tRNA-like sequence to direct BMV-specific RNA synthesis in vitro.

The invention will be further described by the following Examples.

EXAMPLE 1

BMV is a positive strand RNA virus and is the type member of the bromovirus group of plant viruses in the alphavirus-like superfamily of positive-sense RNA viruses. Monocistronic RNA1 and RNA2 encode proteins 1a (containing putative methyltransferase and helicase domains) and 2a (containing polymerase-like domains), respectively. In conjunction with cellular proteins, e.g., eIF3, 1a and 2a compose the template-specific BMV RdRp. The dicistronic RNA3 encodes the 3a movement protein and the coat protein, whose translation is directed by the subgenomic RNA4 (0.88 kb). Synthesis of subgenomic RNA4 is by internal initiation from a (−)-strand copy of RNA3.

The BMV RdRp complex is integrated into plant membranes but can be solubilized with high-concentration-salt and nonionic detergents, such as Triton X-100. The BMV RdRp has been highly enriched and can specifically synthesize minus-strand RNA from input plus-strand RNA templates in a sequence-specific manner. In addition, the BMV RdRp can also synthesize subgenomic plus-strand RNA 4 by initiating with a guanylate residue internally within the minus-strand of RNA 3. The synthesis of minus-strand RNA initiates from the conserved 3' ends of plus-strand BMV RNAs. This conserved region can fold into a tRNA-like structure. As in tRNAs, the terminal three residues are 5'-CCA-3'. Initiation of minus-strand synthesis was reported to begin at the penultimate cytosine residue, making the first nucleotide of the newly synthesized RNA a guanylate.

BMV RNA synthesis is amenable to biochemical studies because the viral RdRp can use exogenously added templates containing BMV promoter sequences. Accurate initiation of (−)-strand RNA synthesis from input (+)-strand templates has been demonstrated. Several steps in (−)-strand RNA synthesis have been defined, including initiation, primer-induced RNA synthesis, the synthesis of abortive initiation products of up to 8 nts accumulating at a 10-fold molar excess to full-length RNA (Sun et al., 1996) and the transition of the RdRp from initiation to elongation (Sun & Kao, 1997a, 1997b). In contrast, the mechanism of subgenomic RNA synthesis has not been carefully studied. Short regions of (−)-strand RNA3 have been employed to refine previous characterizations of the subgenomic promoter and determine how the RdRp recognizes the promoter (Adkins et al., 1997; Siegel et al., 1997). As described hereinbelow, the mechanism of subgenomic (+)-strand RNA synthesis, including initiation and termination, is discerned and compared to (−)-strand synthesis.

Results

Accurate Subgenomic Initiation.

To determine the recognition elements contained within the subgenomic core promoter, a 33 nt proscript (−20/13) was constructed which contains the WT promoter sequence 20 nt 3' of the subgenomic initiation start site in (−)-strand RNA3. This proscript directs the synthesis of a 13-nt product, the first 11 nt of which are BMV sequence followed by two guanylates added by T7 RNA polymerase to allow labeling of RdRp products with [$\alpha$-$^{32}$P]CTP. The BMV sequence within proscript −20/13 is complementary to the viral (+)-strand RNA3 from positions 1,222 to 1,252 and serves as the WT control.

Various mutations within the promoter sequence were created. Initially, transversions, in groups of three nucleotides, were synthesized to scan the entire promoter and determine which regions were required for RNA synthesis. Positions −17 to −9 were identified as containing essential nucleotides because mutations in this region of the promoter reduced the ability of the BMV RdRp to initiate synthesis of subgenomic RNA to about 2% of WT activity. Mutations at nucleotide positions −5 to −3 had a lesser effect, retaining 16% of WT activity. The three nucleotide transversions covering all other positions of the core promoter each only reduced synthesis by 50%. The predominant RdRp product from all templates was 14 nt due to the nontemplated addition of one nucleotide, a phenomenon common to all DNA-dependent RNA polymerases and the poliovirus RdRp.

Unexpectedly, subgenomic synthesis was relatively unaffected by replacement of nucleotides from −2 to the initiation site, +1. Previous work has demonstrated that the identity of the initiating cytidylate for the subgenomic RNA4 must be maintained. The three nucleotide transversion in the −2+1 proscript places a cytidylate at position −1 and it is conceivable that the BMV RdRp is able to utilize this nucleotide for initiation of RNA synthesis directing a product of the same size as the WT proscript by either facilitating the use of a nontemplated guanylate (instead of the templated cytidylate at the +1 position) or bypassing the +1 position completely. To test whether the initiation position can be moved, two additional proscripts were made. Proscript +1C/G specifically replaces the initiating cytidylate with a guanylate while leaving all other positions as WT sequence. Proscript −1/+1 G inserts a guanylate into the initiation site and moves the WT +1 cytidylate into the +2 position. This proscript encodes a 14 nt product (15 nt with nontemplated addition) if the inserted guanylate at the +1 position is recognized by the BMV RdRp. However, if the initiation site can be shifted to the cytidylate now occupying the +2 position, then a 13-nt product (14 nt with nontemplated addition) should be observed. Accurate initiation of the RdRp products can be verified by withholding GTP which is required only for initiation or by treatment with RNase T1 which specifically cleaves after guanylates. Thus, a correctly initiated RdRp product will decrease by 1 nt after RNase T1 digestion.

The RdRp products from proscripts −2+1, −1/+1 G, and WT −20/13 were all initiated with GTP as judged by the reactions lacking GTP and by RNase T1 treatment and are the same size (13 and 14 nt) as T7 size markers. However, no product was synthesized from the +1 G/G prescript. Thus, a cytidylate residue is required as the initiating nucleotide, confirming with earlier observations. It appears that the BMV RdRp can recognize a cytidylate at either one nucleotide 3' or 5' proximal to the original initiation site. All of the reactions demonstrate accurate initiation and validate the use of this system for characterization of the RdRp-subgenomic core promoter interaction. These experiments also confirm that the addition of the nontemplated nucleotide generating the 14-nt product occurs at the 3' end of the (+)-strand product.

Nucleotides Critical for Initiation of Subgenomic RNA Synthesis.

Data from the three nucleotide transversion indicated that positions −17 to −9 contain nucleotides important for RNA synthesis. To identify the critical residues, proscripts that contain single nucleotide transversions at each position within this region and at positions −5 to −3 of the subgenomic core promoter were constructed. Positions −17, −14, −13, −1, −10, and −5 were important for synthesis because transversions significantly decreased RNA synthesis by the BMV RdRp. The most critical positions, −17, −14, −13, and −11, all had activities below 3% of the WT prescript. Changes at positions −10 and −5 were less severe, retaining 31% to 18% of WT synthesis. As a negative control, no synthesis was observed from a prescript, +1 C/G, which contains a transversion at position +1.

Proscripts containing all possible nucleotide replacements at the most critical positions, −17, −14, −13, and −11, were assayed to test the sequence specificity of these four positions. A change of the WT guanylate to uridylate (−17 G/U) at position −17 supported RNA synthesis at 13% of WT activity. Other nucleotide substitutions at −17 (−17 G/C and −17 G/A) were unable to direct RNA synthesis. Nucleotides other than the WT sequence at positions −14 or −13 did not retain appreciable activity, demonstrating the importance of the adenylate at −14 and the cytidylate at −13. A change at position −11 of the WT guanylate to either uridylate or adenylate (−11 G/U or −11 G/A) retained about 8% activity, whereas the original −11 G/C proscript had only 1% of the activity of the WT prescript. To further demonstrate the specific requirements of the above four positions, the WT guanylate at position −10 was replaced with either a uridylate or adenylate without detrimental effects. In fact, both of these mutants, −10 G/U and −10 G/A, resulted in slightly better promoters than the WT prescript, generating 140% of the product of −20/13. These results demonstrate nucleotide specificity at positions −17, −14, −13, and −11 of the BMV subgenomic core promoter.

Examination of the functional moieties of the base in the replacement nucleotides which displayed partial activity suggests contact sites recognized by the BMV RdRp. To test this idea, competition experiments were performed to determine if proscripts −20/13, −17 G/C, and −17 G/U would affect synthesis from a second prescript with the WT promoter sequence directing synthesis of a 15 nt product (designated −20/15). The concentration of the competitor templates was varied from 0.1- to 10-fold molar excess of the −20/15 prescript. Competition was visualized by a decreasing amount of the 15-nt product with a concurrent increase of the 13-nt product. As expected, proscript −20/13 competed efficiently for synthesis because it also contains a WT subgenomic promoter. Synthesis from −20/15 was reduced 50% when −20/13 was present in an equimolar amount. In contrast, proscript −17 G/C was not an effective competitor, decreasing synthesis from −20/15 by only 15% when present at an equimolar ratio. The −17 G/U prescript inhibited synthesis from −20/15 at a reduced level (35%) from that observed with −20/13. This level of inhibition is consistent with the result that synthesis from this mutant template was diminished but not abolished. The result from this experiment is consistent with the idea that position −17, and most likely the other key nucleotides identified by mutagenesis, is contacted by the BMV RdRp.

Alphaviral Subgenomic Promoters.

Figure 10:
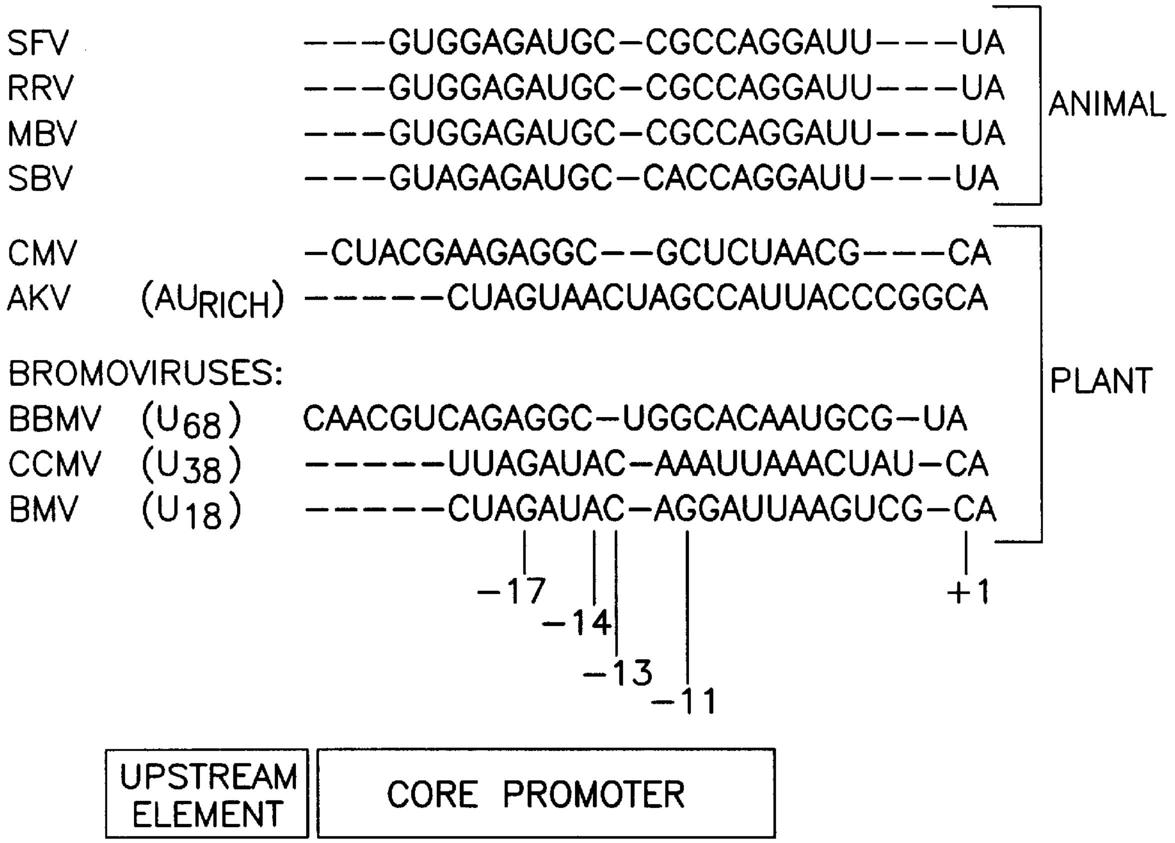
FIG. 10. Alignment of subgenomic promoters from both animal and plant viruses in the alpha-virus like superfamily. Conserved nucleotides in the core promoter are shown in bold. Sequences were obtained from Genbank. Homopolymeric upstream elements, where present, are indicated with brackets. SFV, Semliki Forest Virus (SEQ ID NO:12); RRV, Ross River Virus (SEQ ID NO:13); MBV, Middelburg virus (SEQ ID NO:14); SBV, Sindbis virus (SEQ ID NO:15); CMV, cucumber mosaic virus (SEQ ID NO:16); AMV, alfalfa mosaic virus (SEQ ID NO:17); BBMV, broad bean mottle virus (SEQ ID NO:18); CCMV, cowpea chlorotic mottle virus SEQ ID NO:19); BMV, brome mosaic virus (SEQ ID NO:20). The alignment was generated using the CLUSTALW software program.

A comparison of the BMV subgenomic promoter with those of other members of the alphavirus-like superfamily, infecting both plants and animals, reveals a striking conservation of the four nucleotides critical for synthesis by the BMV RdRp. In addition, all of these promoters contain a pyrimidine as the initiating nucleotide (uridylate in animal viruses and either a cytidylate or uridylate in plant viruses) with a highly conserved adenylate at the +2 position (see FIG. 10). This similarity implies that RdRps from members of the alphavirus-like superfamily recognize subgenomic promoters by a conserved mechanism.

To examine the possibility that the mode of template recognition is conserved, a proscript containing the subgenomic promoter from SFV was constructed and tested its ability to be recognized by the BMV RdRp. So that the RNA product can be visually distinguished from the 13-nt product generated from the BMV proscript, the SFV proscript was designed to direct synthesis of an 11-nt product, the first 9 nt of which are WTSFV sequence followed by two guanylates added by T7 RNA polymerase to allow labeling of RdRp products with [$\alpha$-$^{32}$P]CTP. The SFV proscript directs the BMV RdRp to synthesize a product which is dependent upon ATP, used only as the initiating nucleotide for subgenomic synthesis from this template. The amount of synthesis was only 0.25% of the synthesis from an equimolar amount of WT −20/13 but significantly above background. This result demonstrates a heterologous interaction between an RdRp from a plant-infecting virus with an RNA template containing the subgenomic promoter from an animal-infecting virus.

Discussion

Although initiation of subgenomic RNA synthesis has been studied in other RNA viruses, a detailed characterization of the promoter sequences directing synthesis has not been determined. More than 30 mutations in the BMV subgenomic core promoter were constructed to define the elements required for recognition by the BMV RdRp. Of the 20 nt comprising the core promoter, 4 (−17, −14, −13, and −11) were demonstrated to be essential. Moreover, it was demonstrated that the BMV RdRp can use a cytidylate one position 3' or 5' of the WT initiation site, as well as a uridylate in the case of the SFV promoter. Competition experiments show that a proscript unable to direct RNA synthesis is also unable to inhibit synthesis from a WT proscript, indicating that changes at the four identified positions interfere with the BMV RdRp's ability to bind these mutant templates.

In 1985, Miller et al. demonstrated in vitro synthesis of full-length subgenomic RNA4 using a (−)-strand BMV RNA3 template with its 3' end 20 nt from the initiating cytidylate. Subsequent studies reported that additional sequences flanking the promoter were required for high levels of subgenomic RNA synthesis. Recent work has shown that accurate and efficient RNA synthesis can occur using only the 20 nt comprising the core promoter when directing synthesis of a (+)-stand product fewer than 26 nt in length. Furthermore, a template with its 3' end at position −17 was the smallest promoter capable of directing accurate RNA synthesis, correlating nicely with this study's demonstration of the importance of this position.

Examination of the promoter mutants which partially enabled proscripts to be recognized by the BMV RdRp allow us to predict base-functional groups required for contact by the BMV RdRp. The C6 carbonyl and perhaps the N1 imine of the guanosine at position −17 are implicated as contact sites. Substitution with a uridylate (containing spatially equivalent carbonyl and imine groups) could partially restore this promoter's ability to direct synthesis, as well as partially inhibit synthesis from a WT promoter. The lack of restoration of synthesis with a cytidylate to uridylate change at position −13 suggests the unique amine group at the cytosine C4 position may be required. The guanylate at position −11 could be changed to either an uridylate or adenylate and weakly direct RNA synthesis. These results indicate that the C6 carbonyl group and the N7 imine group both contribute to the interaction with the BMV RdRp. For position −14, several contact sites may be needed. The stringent requirements for these nucleotides may be largely responsible for the template specificity exhibited by the BMV RdRp.

The nucleotides identified as crucial for RNA synthesis in the BMV subgenomic promoter are highly conserved in the subgenomic promoters from other members of the alphavirus-like superfamily, implying a common mode of RdRp subgenomic promoter recognition. Accordingly, a proscript containing the animal-infecting SFV subgenomic promoter was able to direct accurately initiated RNA products using the GMV RdRp. Thus, there is heterologous recognition between an RdRp and RNA template from plant- and animal-infecting viruses.

A sequence-specific mode of recognition is strikingly similar to template recognition by the DNA-dependent RNA polymerases (DdRp). DdRps primarily interact with their respective templates via sequence-specific contacts. For example, the *Escherichia coli* RNA polymerase holoenzyme recognizes the identities of nucleotides at the −10 and −35 regions relative to the transcription start site. The single polypeptide bacteriophage polymerases (T7, T3, and SP6) contact specific nucleotides within a 17-nt consensus promoter primarily at nucleotides −11 to −9. The results of this study suggest that RdRps may discriminate between templates in a fashion analogous to that of DdRps.

Current dogma posits that protein and RNA interact primarily through a structure-specific mode of recognition allowing protein contact with one or more unstructured nucleotides. For example, the bacteriophage R17 coat protein recognizes a hairpin containing the ribosome binding site of the phage replicase. Also, viral RdRps replicating full-length products from linear templates have been shown to require various structures on the 3' end of the RNA template to initiate accurate synthesis. One fundamental difference between genomic and subgenomic RNA synthesis is that subgenomic initiation occurs internally in a manner analogous to DdRps. Therefore, it is quite plausible that template selection by RdRp may proceed in a manner similar to that of DNA recognition by DdRps. Proteins recognizing unstructured RNA in a sequence-specific manner have been reported, including the translational repressor RegA of bacteriophage T4 which specifically recognizes an unstructured 12-nt sequence. RdRp sequence specificity has been suggested previously with the (−)-strand RNA influenza virus. Three nucleotides near the 3' end of the (−)-strand RNA were found to be required for synthesis, although accurate initiation was not demonstrated. Subsequently, these nucleotides were shown to be directly contacted by the influenza RdRp. However, additional data demonstrated the need for sequences located at the 5' end of the influenza RNA which form a partially double-stranded structure recognized by the RdRp.

Although secondary structure may facilitate efficient subgenomic synthesis in full-length (−)-strand RNA3, several lines of evidence suggest that it plays a minor role in the BMV RdRp recognition of the subgenomic core promoter. The predicted hairpin structure in the WT prescript has a low free energy calculation, −0.2 kcal/mol. This hairpin has a predicted melting temperature of 20° C. and would mot likely be denatured under our standard reaction conditions of 30° C. The −5 U/A mutant which strengthens the predicted structure had an adverse effect upon synthesis. Conversely, mutants that altered or obliterated the hairpin had either no (−10 G/U and −9 (U/A) or only a slight (−8-6 triple mutant) effect on synthesis. Enzymatic studies could not determine a stable structure in the WT proscript. A minimal prescript 22 nt in length, lacking any predicted structure, supported accurate initiation. Furthermore, the computer-predicted structure in the location of the initiation nucleotide from the predicted structure of longer proscripts containing additional WT sequences which also directed accurate RNA synthesis. Finally, the specific nucleotides required to direct accurate RNA synthesis reside in a single-stranded region of the predicted structure of the WT (−20/13) proscript. Taken together, these results strongly argue that the BMV RdRp-core promoter interaction occurs primarily by the recognition of specific sequences.

Example 2

For RdRp, the conditions required for the initiation of (−)-strand RNA synthesis have been characterized (Miller et al., 1986; Kao and Sun, 1996). Also, there is an observed increase in the affinity of the association between RdRp and template RNA as RdRp progresses from the initiation of RNA synthesis to elongation (Sun and Kao, 1997).

Materials and Methods

RdRp Activity Assays

BMV RdRp was prepared from infected barley essentially as described by Sun et al. (1996). RdRp preparations used in abortive initiation studies were passed through an additional PD10 (Pharmacia) gel filtration column to remove NTPs and other low molecular weight contaminants. Standard RdRp activity assays consisted of 43 $\mu$L reactions containing 20 mM sodium glutamate (pH 8.2), 4 mM $MgCl_2$, 12 mM dithiothreitol, 0.5% (v/v) Triton X-100, 2 mM $MnCl_2$, 200 $\mu$M ATP, 500 $\mu$M GTP, 200 $\mu$M UTP, 242 nM [$\alpha$-$^{32}$P]CTP (400 Ci/mmol, 10 mCi/mL, Amersham), equal moles (generally 1.0 pmol) template RNA, and 5–10 $\mu$L RdRp. Reactions were incubated 90 minutes at 30° C. unless indicated otherwise. Reaction products were extracted with phenol/chloroform (1:1, v/v) and precipitated with three volumes of ethanol and 10 $\mu$g glycogen following standard protocols (Sambrook et al., 1989). The NTP composition was modified in some experiments as indicated in the figure legends.

Analysis of RdRp Products

Products from RdRp reactions were suspended in 1× denaturing loading buffer (45% (v/v) deionized formamide, 1.5% (v/v) glycerol, 0.04% (w/v) bromophenol blue and 0.04% (w/v) xylene cyanol) and denatured by heating at 90° C. for 3 minutes prior to analysis by denaturing polyacrylamide gel electrophoresis. Products were analyzed on 20% or 24% acrylamide (19:1 acrylamide: bisacrylamide)-7M urea gels (14×14×0.05 cm) according to published procedures (Sambrook et al., 1989). In some cases, a 5% acrylamide stacking gel (2×14×0.05 cm) was used. Products from reactions containing templates directing synthesis of 198 nt or longer products were digested with 2.5 units S1 nuclease (Promega) from 10 minutes at 30° C. Denaturing loading buffer was added to S1-treated products prior to analysis by denaturing polyacrylamide gel electrophoresis on 5% acrylamide gels while native loading buffer (5% (v/v) glycerol, 0.04% (w/v) bromophenol blue, 0.04% (w/v xylene cyanol) was added to S1-treated products prior to analysis by non-denaturing electrophoresis on 1% agarose gels. All gels were exposed to film at −80° C. and the amount of label incorporated into newly synthesized RNAs was determined with a phosphorimager (Molecular Dynamics).

Synthesis of Templates for RdRp

PCR was used to synthesize cDNA copies of either (−)-strand BMV RNA3 encompassing the subgenomic promoter or (+)-strand BMV RNA3 or RNA1 encompassing the (−)-strand promoter. Pairs of synthetic oligonucleotides, one of which contained a T7 promoter, were used in PCR reactions with cDNA clones of BMV RNA3 (pB3TP8) or RNA1 (pB1TP3), respectively (Janda et al., 1987). Thirty cycles of PCR were used for amplification with Taq polymerase, with each cycle consisting of 30 s each of denaturation at 94° C., annealing at 5° C. below the lowest oligonucleotide Tm and elongation at 72° C. PCR products were purified as described above (Sambrook et al., 1989) and used as templates for in vitro transcription. The T7 DdRp was used for all transcription reactions (Ampliscribe, Epicentre) (Table 4). Synthesis of the B3-198 template has been previously described (Sun & Kao, 1997a). Molecular weight markers of 8 and 13 nts were synthesized by the protocol of Milligan et al. (1987) using oligonucleotides T7(+) and T7(−)8mer or T7(−)13mer (Table 4). Transcripts of full-length (−)- and (+)-strand RNA3 were synthesized from plasmids containing the cDNA of RNA3. Transcripts of (−)-strand RNA3 with a 250 nt extension at the 5' end and (+)-strand RNA3 with a 150 nt extension at the 5' end were synthesized from plasmids containing the cDNA of RNA3 positioned 250 or 150 nt downstream of a T7 promoter, respectively.

Prior to RdRp assays, transcripts were purified by anion exchange chromatography on Qiagen tip-20 columns using the manufacturer's protocol. All RdRp templates contain two non-viral guanylates at the 5' end incorporated during initiation of T7 polymerase transcription on the cDNA templates. Concentration of RdRp templates was determined by toluidine blue staining following denaturing PAGE and/or by using a spectrophotometer as previously described (Adkins et al., 1997).

Results

Sequence Requirements for Initiation of Subgenomic RNA Synthesis

BMV subgenomic RNA synthesis in vivo initiates at the (−)-strand complement of nt 1242 of RNA3 using a cytidylate as the first templated nucleotide (Dasgupta & Kaesberg, 1982). Short regions of (−)-strand RNA3 can direct accurately initiated subgenomic synthesis (Adkins et al., 1997). These RNAs are referred to as proscripts to denote the fact that the promoter and template regions are distinct for subgenomic RNA synthesis. To determine the sequence context required for subgenomic initiation, a series of proscripts was synthesized that contained mutations surrounding the subgenomic initiation site and directed BMV RdRp synthesis of 13 nt products. The predominant RdRp product from all functional proscripts was 14 nts due to the non-templated addition of one nucleotide, a phenomenon previously observed with the BMV RdRp (Siegel et al., 1997). Relative percent activity of the mutant proscripts was determined by comparison of the amount of product synthesized from them to that synthesized from wild-type proscripts. All values represent the mean of four independent experiments.

Transversion of the initiation cytidylate to a guanylate was previously shown to abolish the ability of the proscript to direct RNA synthesis (Adkins et al., 1997; Siegel et al., 1997). However, the BMV RdRp can inefficiently initiate synthesis using a uridylate as the first templated nucleotide (Siegel et al., 1997). To address the roles of the neighboring nucleotides, proscripts containing all possible nucleotide replacements at the +2 position were assayed to determine the requirements for this position (FIG. 1A). Mutation of the +2 adenylate to a guanylate abolished the ability of the prescript to direct RNA synthesis while a change to a cytidylate or uridylate directed 37% or 66% of the wild-type level of RNA synthesis, respectively (FIG. 1A and FIG. 1B, lanes 6–8). Thus, an adenylate at the +2 position is preferred for subgenomic RNA synthesis although no predictions can be made for the base moieties required at +2.

The nucleotide requirements at the +3 and +4 positions for BMV subgenomic RNA synthesis were next evaluated. Mutation of the +3 uridylate to a cytidylate or guanylate reduced the ability of the template to direct RNA synthesis to 64% or 58%, respectively, of the wild-type level (FIGS. 1A and 1C). Mutation of the +4 adenylate to a cytidylate had no adverse effect on its ability to direct RNA synthesis (FIGS. 1A and 1C). Mutation of the +4 adenylate to a guanylate reduced the ability of the template to direct RNA synthesis to 57% of the wild-type level (FIGS. 1A and 1C). Thus, the effect of template sequence on RNA synthesis appears to decrease as the distance from the initiation nucleotide increases (FIG. 1A).

The effect of nucleotide changes at the −1 position was also determined. Mutation of the −1 guanylate to an adenylate reduced activity to 82% of the wild-type proscript whereas a change to a uridylate had no effect (FIG. 1A and FIG. 1B, lanes 4, 5), suggesting that the identity of the −1 nucleotide does not affect the efficiency of subgenomic RNA synthesis. Quite interestingly, synthesis of RdRp products from alternate initiation sites in proscripts containing −1 mutations was observed, albeit at less than 5% of the amount from the authentic initiation site (FIG. 1B, lanes 4, 5). The novel 15 nt RdRp product from prescript −1G/U was apparently initiated at the −1 position using a templated uridylate. The novel 16 nt RdRp product from proscript −1G/A was apparently initiated at the −2 cytidylate. In proscript −1G/A, the −2 and −1 nts are now cytidylate-adenylate, the sequence also found at the +1 and +2 positions. These results demonstrate that there is some flexibility in recognition of the initiation site by RdRp.

Relaxed Requirement for the +2 nt for (−)-Strand Synthesis

To examine whether the +2 nt in the promoter for (−)-strand synthesis had a similar preference, two templates were used (B1-242+2 C/A and B1-242+2C/U). Each template directed synthesis of a 242 nt (−)-strand RNA1 product containing a change of the +2 cytidylate to an adenylate or uridylate. Synthesis from B1-242+2 C/A or B1-242+2 C/U was compared with synthesis from a second template (B3-198), which directed synthesis of a 198 nt (−)-strand RNA3 product, present at the same molar concentration in the same reaction. A change of the +2 cytidylate to a uridylate reduced synthesis to 31% (similar to that previously observed by Sun et al., 1996) while a change to an adenylate increased synthesis to 157% of wild-type B1-242 and B3-198. This result suggests that the identity of the +2 nt for (−)-strand synthesis is not as critical as it is for subgenomic synthesis.

High UTP Concentration Is Required for Subgenomic RNA Synthesis

A requirement for high GTP concentration during (−)-strand RNA synthesis was previously observed (Kao & Sun, 1996). The preference for a +2 adenylate (noted above) and the inefficient synthesis of subgenomic RNA in vitro when [α-$^{32}$P]UTP is used as the radiolabel instead of the usual [α-$^{32}$P]CTP suggested that the second nucleotide incorporated during subgenomic RNA synthesis (UTP) may also have special requirements. To examine this possibility, the UTP requirement for subgenomic and (−)-strand RNA synthesis was compared using up/45 (directing synthesis of a 207 nt subgenomic RNA) and B3-198. Both RNAs were used by the BMV RdRp when present individually in reactions containing 50 μM UTP (FIG. 2, lanes 2, 3). Furthermore, an equimolar mixture of the two RNAs in reactions containing 50 μM UTP yielded very similar amounts of products (FIG. 2, lane 4) to the reactions containing either RNA alone (FIG. 2, lanes 2, 3) demonstrating approximately equal promoter use by the BMV RdRp. Reduction of the UTP concentration to 1.6 μM decreased synthesis from both templates but by different amounts. In three independent experiments, subgenomic RNA synthesis was reproducibly more diminished than (−)-strand synthesis by 4–10 fold. In the experiment shown (FIG. 2, lanes 5, 6), (−)-strand synthesis was reduced to 13% of the levels observed at 50 μM UTP while subgenomic synthesis was reduced to undetectable levels. These results provide additional evidence for the preference of a +2 adenylate in the template for subgenomic RNA synthesis and suggest that the synthesis of the phosphodiester bond in subgenomic RNA requires high concentrations of both GTP and UTP.

Differential Primer Use During Subgenomic and (−)-Strand Genomic RNA Synthesis

Figure 3:
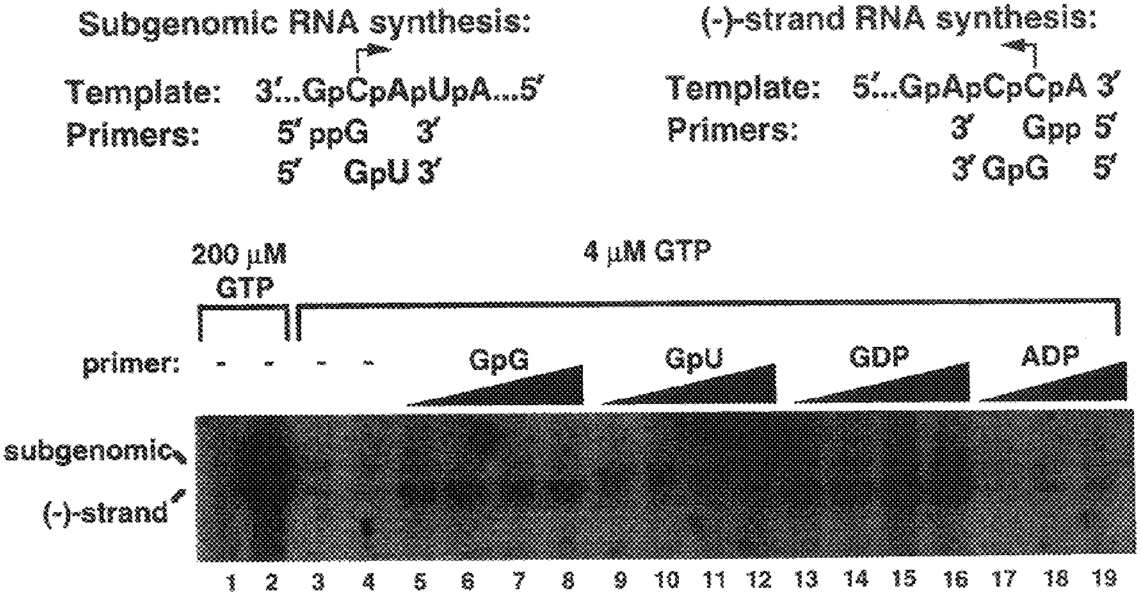
FIG. 3. Differential primer use during subgenomic and (−)-strand RNA synthesis. Sequences surrounding the initiation sites (indicated with arrows) in templates for subgenomic (up/45; directing synthesis of a 207 nt subgenomic RNA) and (−)-strand (B3198; directing synthesis of a 198 nt (−)-strand RNA3) synthesis are shown above relevant primers. Products from RdRp reactions were analyzed by electrophoresis on a 5% denaturing polyacrylamide gel followed by autoradiography. An equimolar mixture of templates was included in all reactions except the control reaction (to which no template was added) whose products are shown in lane 1. Lane 2 contains the products from a standard reaction. Lanes 3–19 contain the products synthesized at 4 μM GTP with the addition of the primers indicated above the autoradiograph. Primer concentrations included in RdRp reaction were 250 μM (lanes 5, 9, 13, and 17), 500 μM (lanes 6, 10, 14, and 18), 1000 μM (lanes 7, 11, 15, and 19) and 1250 μM (lanes 8, 12, and 16). Positions of the subgenomic and (−)-strand products are indicated to the left of the autoradiograph.

Differences in the roles of the +2 nt for subgenomic and (−)-strand synthesis prompted the comparison of the use of the initiation nucleotide for these two types of RNA synthesis. Since GTP is used to initiate both subgenomic and (−)-strand RNA synthesis, the effect of GTP concentration on both types of synthesis was analyzed. No difference was observed in subgenomic and (−)-strand RNA synthesis with each first being detected at 25 μM and continuing to increase through 200 μM GTP. Next, the ability of mono- or dinucleotide primers to replace GTP as the initiation nucleotide was examined. Primers have been previously demonstrated to alleviate the need for high concentrations of GTP (Kao & Sun, 1996). Primer GpU is complementary to the initiation sequence for subgenomic RNA synthesis while GpG is complementary to the initiation sequence for (−)-strand RNA synthesis as shown in FIG. 3. GDP is expected to serve as a primer for both subgenomic and (−)-strand RNA synthesis.

Control reactions contained 200 μM GTP and equimolar mixtures of templates for subgenomic (up/45) and genomic (−)-strand (B3–198) synthesis and resulted in synthesis of approximately equal molar amounts of subgenomic and (−)-strand products (FIG. 3, lane 2). When GTP was reduced to 4 μM, synthesis of both subgenomic and (−)-strand products decreased to 1.5% of that observed at 200 μM GTP (FIG. 3, lanes 3, 4). The addition of GpG to reactions to final concentrations of 250–1250 μM (FIG. 3, lanes 5–8, respectively) stimulated (−)-strand synthesis from 7 to 10-fold over the basal level while subgenomic RNA synthesis remained unchanged. The addition of GpU to reactions at the same concentrations (FIG. 3, lanes 9–12) stimulated subgenomic synthesis by about 3-fold over the basal level while (−)-strand synthesis was unchanged. The reduced stimulation of subgenomic as compared to (−)-strand RNA synthesis is consistent with previous observations (Kao & Sun, 1996). The subgenomic product reproducibly migrated to a lower position when primed with GpU, perhaps due to the lack of 5' phosphates on the dinucleotide primed product. The addition of GDP to reactions at 250–1250 μM stimulated synthesis of subgenomic RNA by 1.2 to 3.4 fold and (−)-strand by 9.4 to 19 fold (FIG. 3, lanes 13–16). ADP was added at 250–1000 μM (FIG. 3, lanes 17–19) and resulted in a 1.7-fold stimulation of (−)-strand synthesis at the 1000 μM level (FIG. 3, lane 19) while no detectable increase in subgenomic synthesis was observed at any level. These results demonstrate that mono- and dinucleotide primers stimulate (−)-strand genomic RNA synthesis more than subgenomic RNA synthesis under conditions of limiting GTP. Furthermore, these results confirm the observation that the initiation of subgenomic and (−)-strand RNA synthesis has different requirements.

Abortive Initiation During Subgenomic RNA Synthesis

Figure 4A:
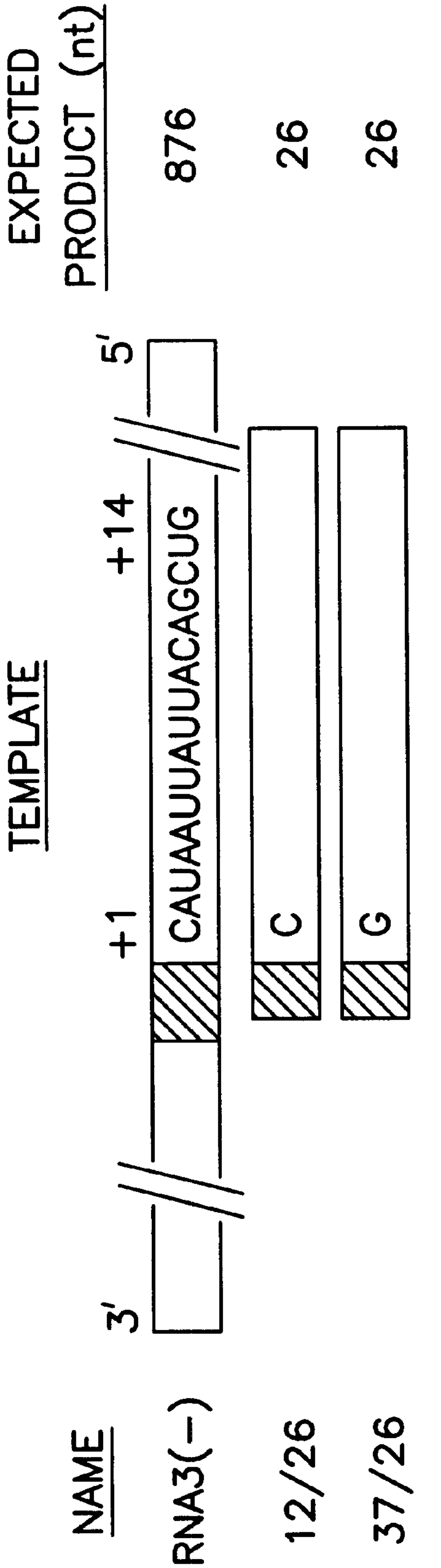
FIG. 4. (A) Diagrams of the three RNAs used in RdRp assays. Full-length (−)-strand RNA3 (RNA3(−)) and proscript 12/26 should direct RNA synthesis while proscript 37/26 has a mutated initiation site. The shaded box represents the location of the polyuridylate tract. The sequence of the first 14 nts (SEQ ID NO:21) of all three templates is shown on RNA3(−) and the length of excepted RdRp products is shown on the right.
Figure 4B:
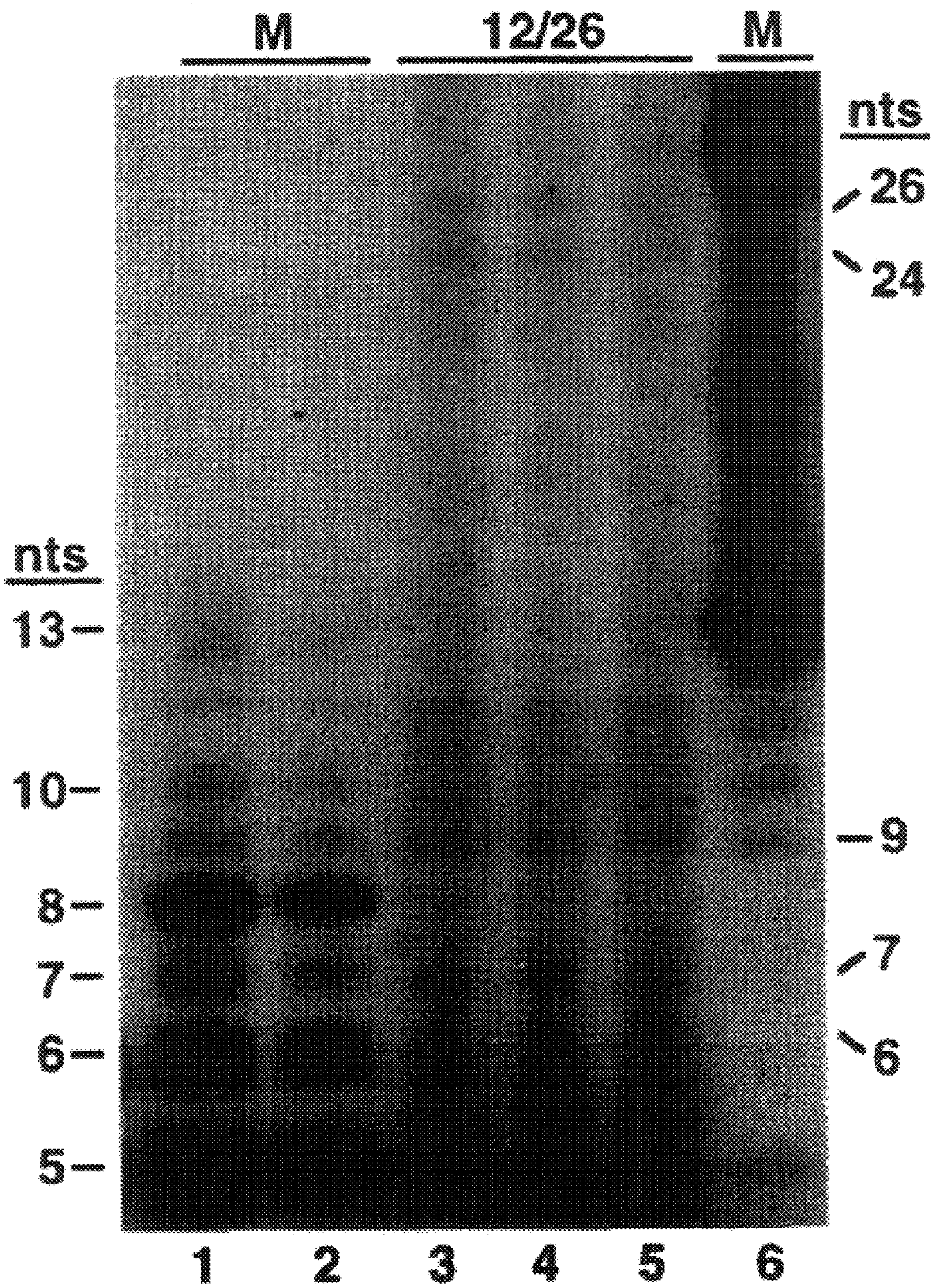
Figure 4C:
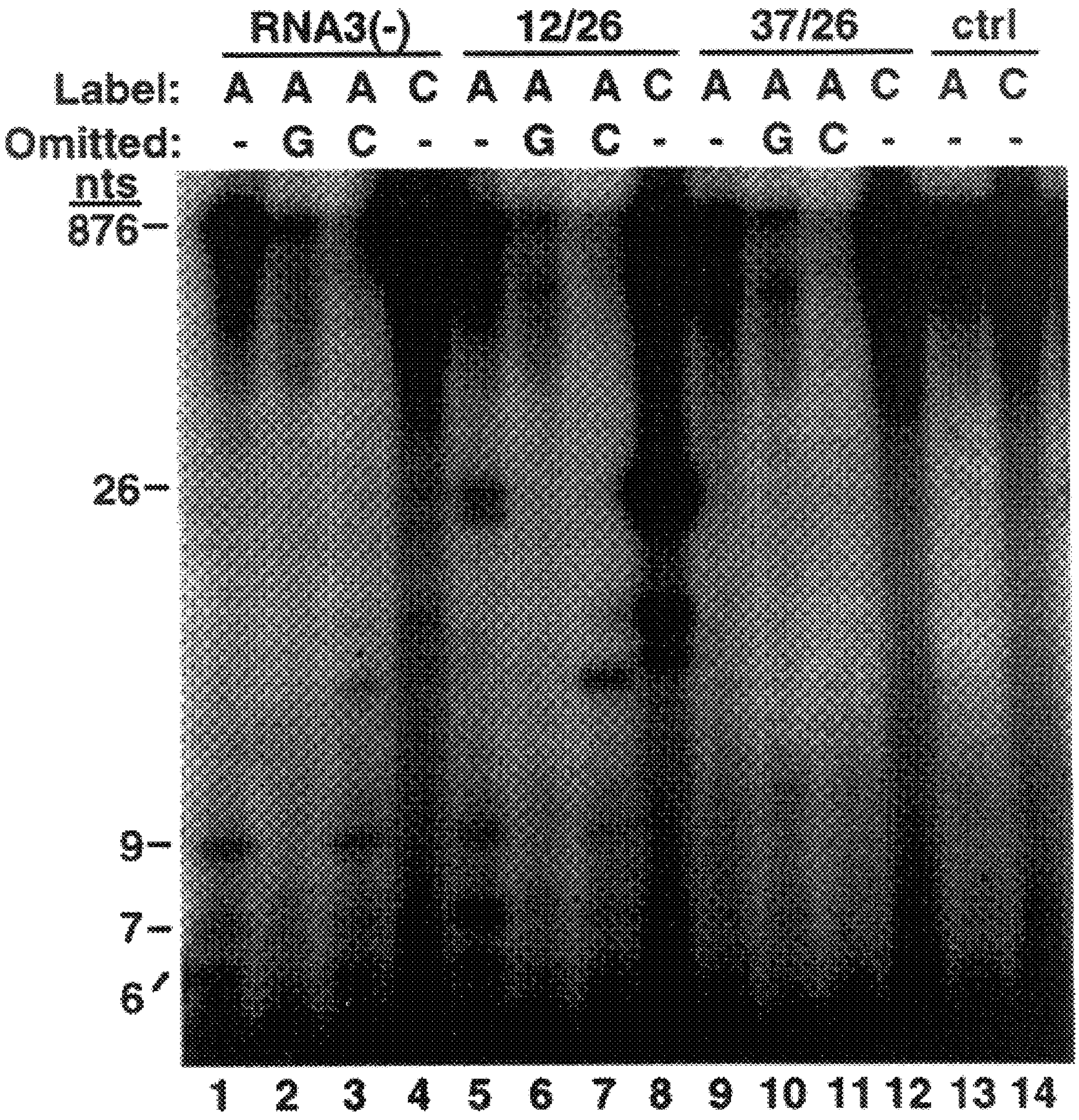

Synthesis of abortive products during initiation of (−)-strand synthesis was previously observed (Sun et al., 1996; Sun & Kao, 1997b). Since (−)-strand synthesis initiates near the 3' end of the genomic RNA, it is of interest to determine whether abortive initiation occurs during initiation from an internal promoter. Thus, the products of subgenomic RNA synthesis reactions were analyzed for the presence of oligonucleotides (potentially representing abortive initiation products) using high resolution polyacrylamide gels. [α-$^{32}$P]ATP was used as a label in these experiments due to the lack of cytidylates in the expected product prior to position +14 (FIG. 4A) and the inefficient labeling observed with UTP (noted above). Greater synthesis of full-length products was consistently observed with [α-$^{32}$P]CTP than with [α-$^{32}$P]ATP, perhaps due to ATP hydrolysis by the BMV 1a helicase-like protein, a component of RdRp (compare FIG. 4C, lanes 1 and 4, and lanes 5 and 8). Several sizes of oligonucleotides were observed during synthesis from proscript 12/26 (containing an 8 nt polyuridylate tract and directing synthesis of a 26 nt subgenomic product) (FIG. 4A; FIG. 4B, lanes 3–5; FIG. 4C, lane 5) and also during synthesis of full-length subgenomic RNA from (−)-strand RNA3 (FIG. 4C, lane 1). The oligonucleotides were 6, 7, and 9 nts in size by comparison to the T7 DdRp-generated RNAs of the sequences 5' GUAUUA 3', 5' GUAUUAA 3' and 5' GUAUUAAUA 3' (FIG. 4B). The RdRp-produced oligonucleotides of 6, 7 and 9 nt were in 12, 7 and 3-fold molar excess, respectively, to the full-length 26 nt product and in 20, 8 and 7-fold molar excess, respectively, to the full-length subgenomic RNA as determined by phosphorimager quantitation. Other sizes of oligonucleotides were present but observed less reproducibly.

While some endogenous BMV RNA was present in the RdRp preparation and directed synthesis of high molecular weight products in the absence of added template, no oligonucleotides were synthesized unless a (−)-strand RNA3 template was added (FIG. 4C, lanes 13, 14). The oligonucleotide products were judged to be correctly initiated based on the following lines of evidence. Labeling of both oligonucleotides and full-length products was significantly reduced or eliminated when GTP, the initiating nucleotide, was omitted from the reactions (compare FIG. 4C, lanes 2, 6 with lanes 1, 5). Correctly initiated RNAs do not contain a cytidylate until position +14. Thus, abortive products should lack cytidylates. It was found that oligonucleotide synthesis was unaffected when CTP was omitted from reactions while synthesis of full-length products was abolished (although some higher molecular weight products, 14 and 17 nts, were seen presumably due to contaminating CTP) (compare FIG. 4C, lanes 3 and 7 with lanes 1 and 5). Full-length products and some potential pause products were labeled using [α-$^{32}$P]CTP while the oligonucleotides were not (compare FIG. 4C, lanes 4 and 8 with lanes 1 and 5). Finally, a proscript (37/26) containing a transversion of the +1 cytidylate to guanylate failed to direct synthesis of either oligonucleotide or full-length products (FIG. 4C, lanes 9–12).

Figure 4D:
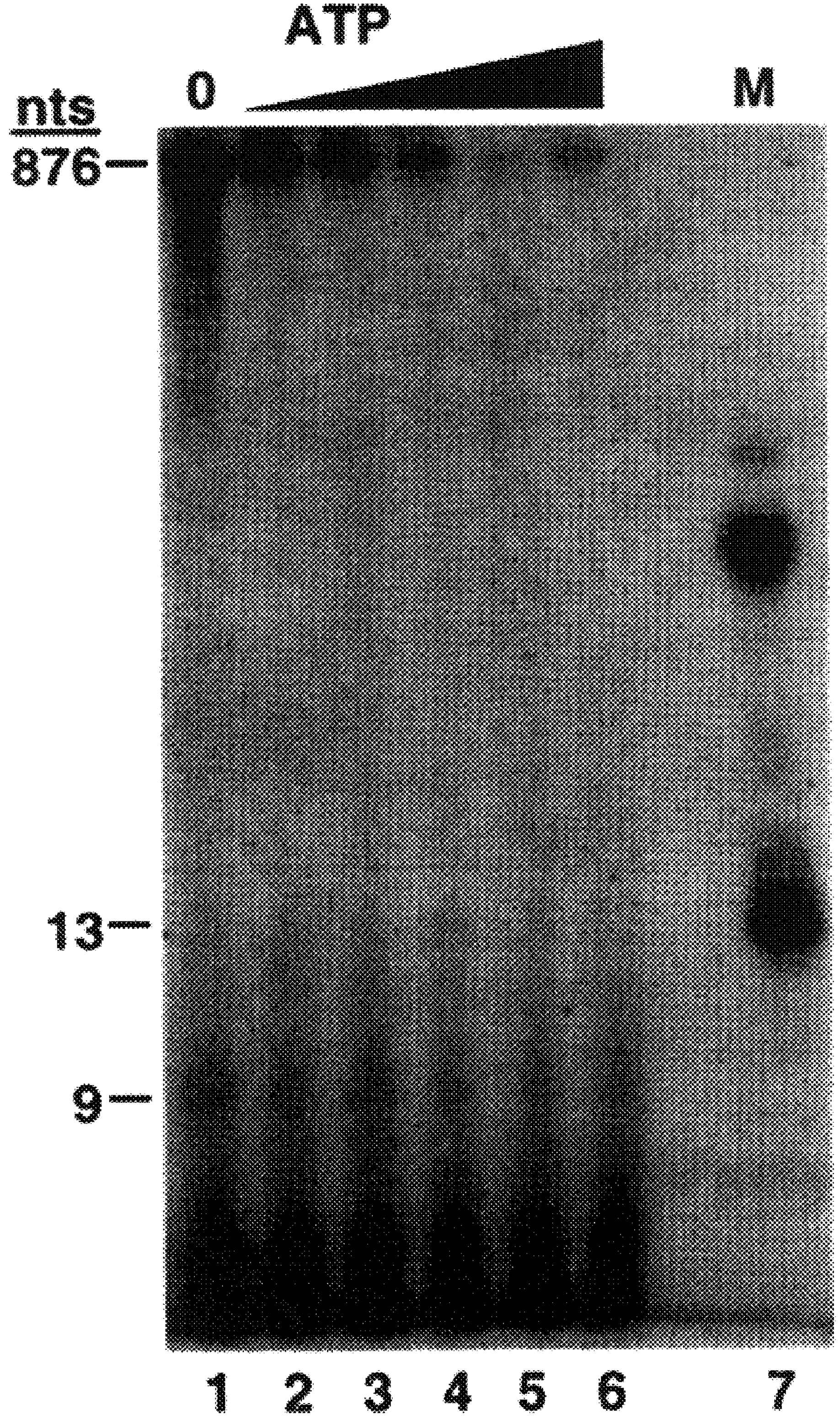

Both the full-length 26mer and a prematurely terminated 24mer were observed from the 12/26 template when [α-$^{32}$P]ATP was used as label (FIG. 4B, lanes 3–5; FIG. 4C; lane 5). This is likely due to limiting ATP (242 nM) in the form of [α-$^{32}$P]ATP. This observation raised the concern that limiting ATP might be responsible for the production of the oligonucleotides. To examine this possibility, successively higher concentrations of unlabeled ATP were added to RdRp reactions. Synthesis of the oligonucleotides and elongated products responded in a similar manner to the addition of increasing amounts of unlabeled ATP (FIG. 4D). The 9 nt RNA and elongated products were detectable when the ATP concentration was increased to 30 $\mu$M indicating that the synthesis of oligonucleotides is an innate property of the BMV RdRp and not due simply to limiting substrates (FIG. 4D).

Figure 4E:
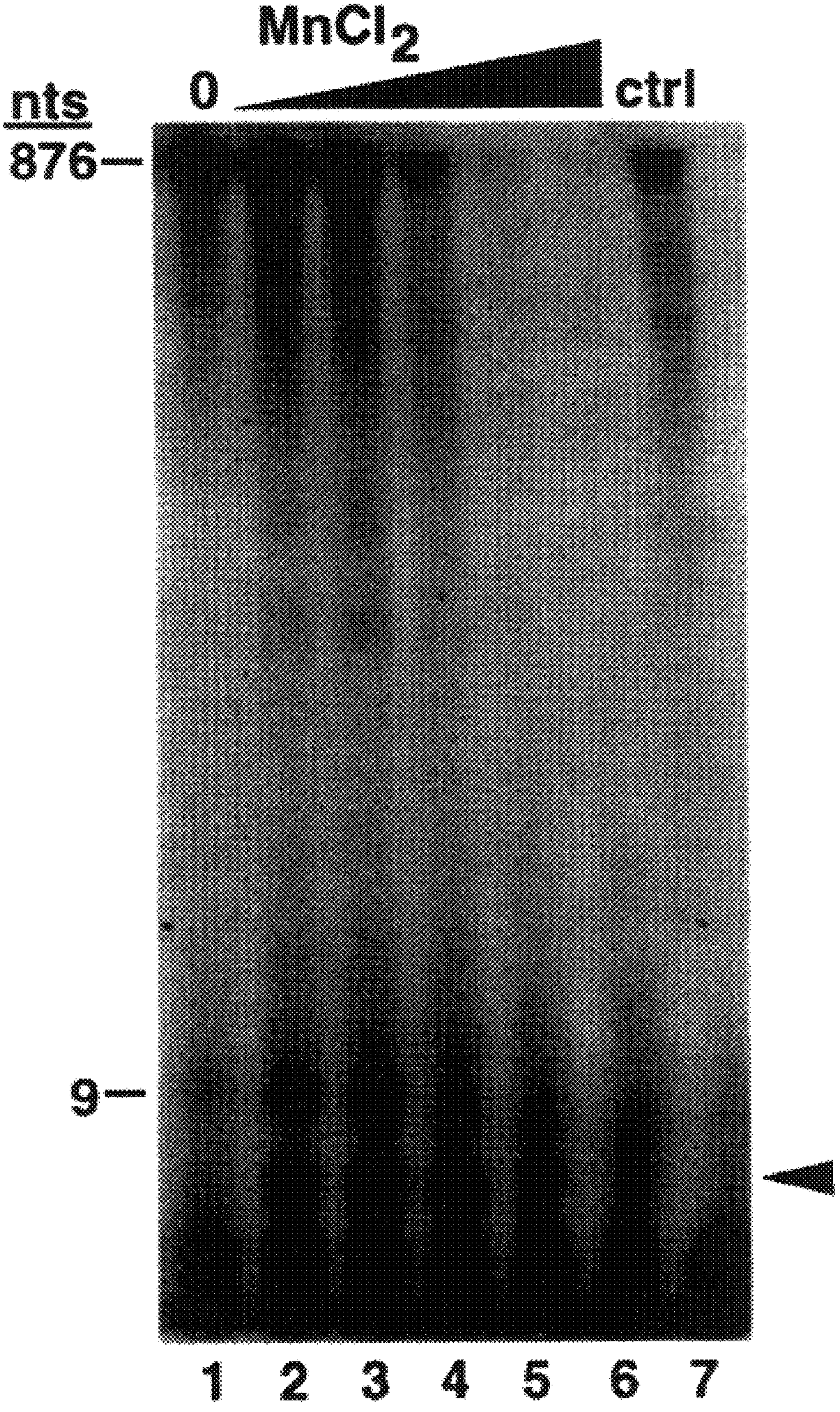

Magnesium is required for the elongation phase of (−)-strand RNA synthesis while manganese suffices for initiation (Sun et al., 1996). The effect of manganese on the synthesis of oligonucleotide and full-length products from the subgenomic promoter was examined (FIG. 4E). At 1 to 2 mM, $MnCl_2$ increased synthesis of full-length products by 8–28% and the synthesis of the 9 nt RNA by 95–127%. Addition of $MnCl_2$ to more than 2 mM reduced synthesis of both oligonucleotides and elongated products although elongated products were more sensitive at lower $MnCl_2$ concentrations (FIG. 4E; lanes 4–7). The addition of $MnCl_2$ also resulted in the appearance of a novel oligonucleotide product (compare FIG. 4E, lanes 1 and 2–4). These results correspond to previous observations for initiation of (−)-strand RNA synthesis (Sun et al., 1996).

Figure 5A:
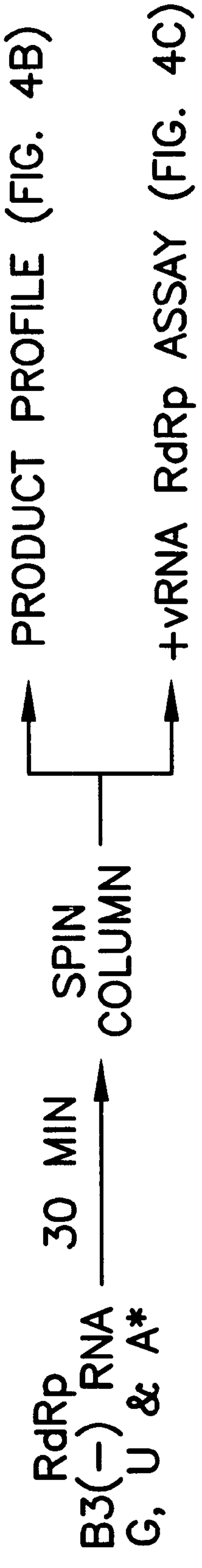
FIG. 5. (A) Protocol for experiment. RdRp reactions (100 $\mu$l) lacking CTP were incubated for 30 minutes at 30° C. before being applied to a Sephadex CL-6B spin column equilibrated in 1× RdRp buffer lacking NTPs. Sixteen 100 $\mu$l fractions were collected, split into two aliquots and analyzed for RdRp products (B) or RdRp activity (C).
Figure 5B:
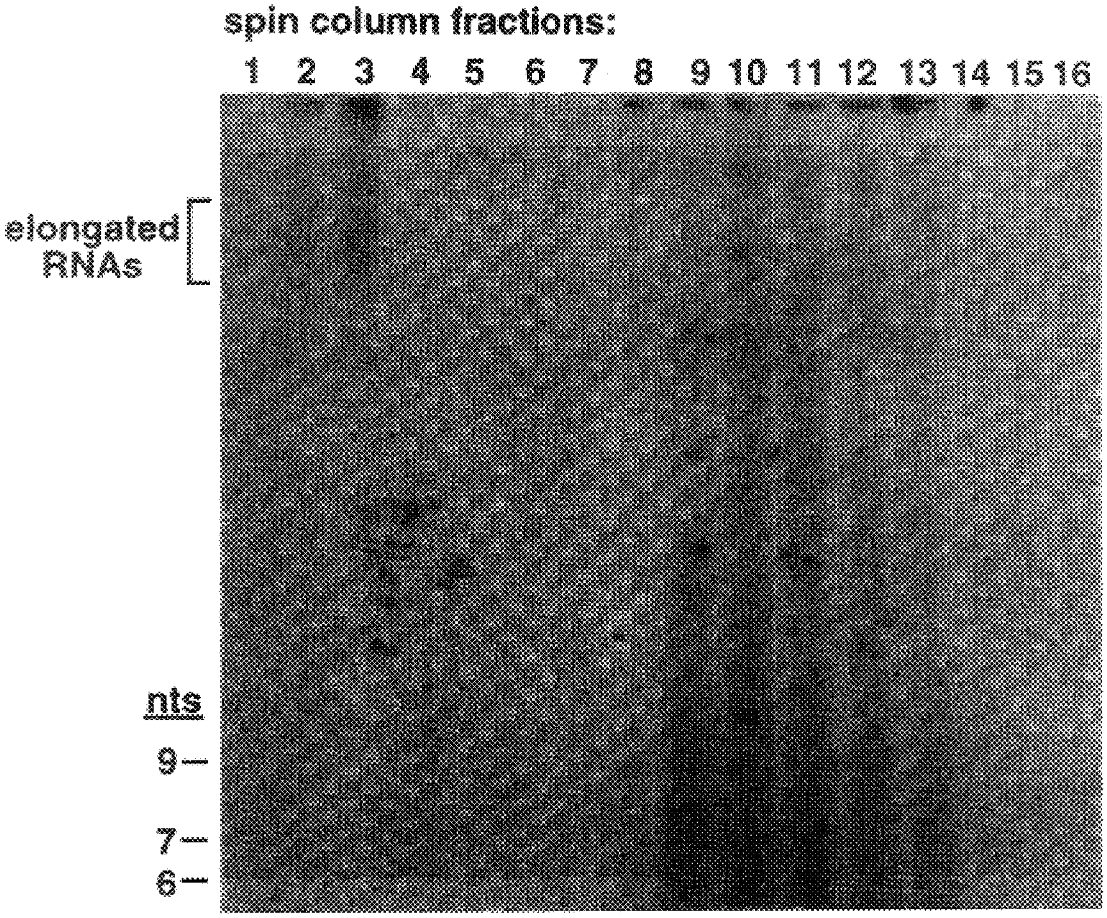
Figure 5C:
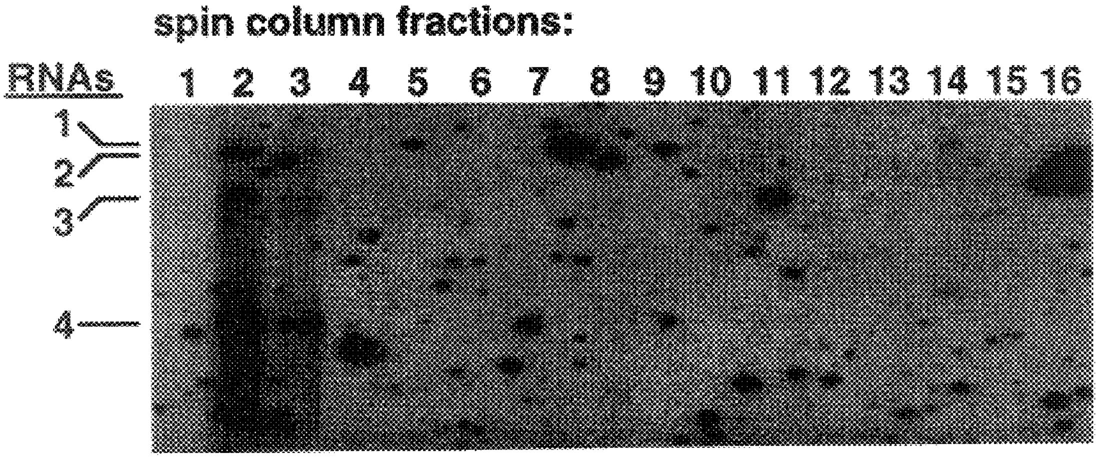

To determine whether the oligonucleotides produced during subgenomic RNA synthesis were released by RdRp and thus represented abortive products, the following experiments were conducted. Reactions lacking CTP should arrest RdRp on the template RNA. These arrested complexes were fractionated by passage through Sephadex CL-6B spin columns. Sixteen consecutive fractions were collected and divided into two sets, one of which was analyzed for RNA products and the second of which was assayed for RdRp activity. Elongated RNAs and RdRp activity were found in fractions 2 and 3 while the 6, 7 and 9 nt oligonucleotides were found in fractions 8 to 13 (FIGS. 5B and 5C). These results demonstrate that the elongated RNAs remain in a ternary complex with the RdRp while the oligonucleotides are released from the RdRp complex and hence represent the products of abortive initiation.

Termination of BMV RNA Synthesis

Figure 6A:
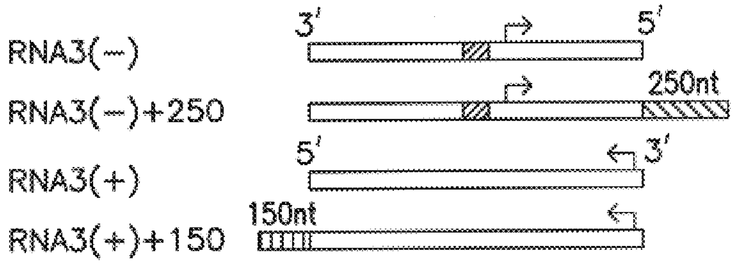
FIG. 6. (A) Templates used for the experiments shown in (B) and (C). RNA3(−) (wild type (−)-strand RNA3) and RNA3(−)+250 ((−)-strand RNA3 with a 250 nt 5' extension of plasmid origin (diagonal stripes)) were used to examine termination of subgenomic RNA synthesis. RNA3(+) (wild type (+)-strand RNA3) and RNA3(+)+150 ((+)-strand RNA3 with a 150 nt 5' extension of plasmid origin (vertical stripes)) were used to examine termination of genomic (−)-strand synthesis. The locations of the extensions (hatched boxes), initiation sites (arrows) and polyuridylate tracts (shaded boxes) are indicated.
Figure 6B:
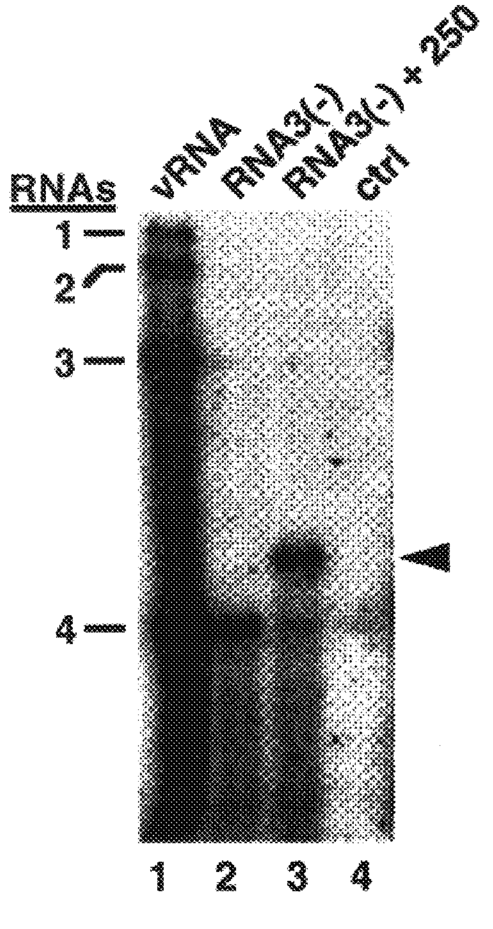
Figure 6C:
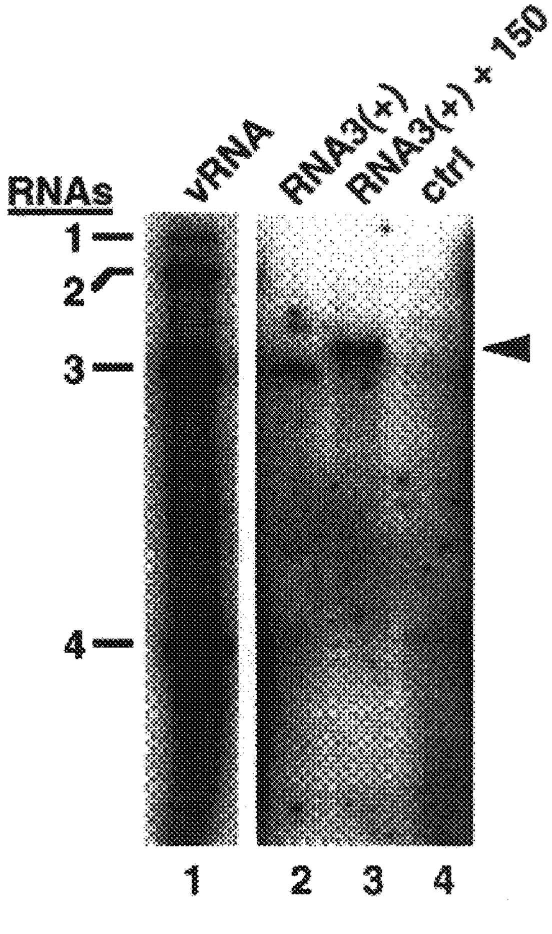
Figure 7:
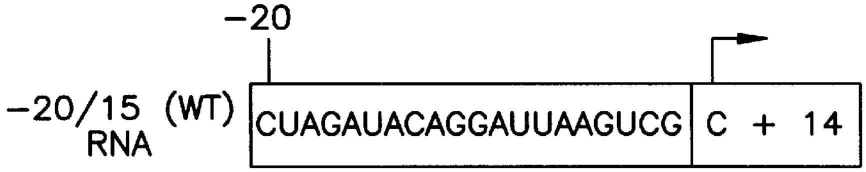
FIG. 7. $I_{50}$ values of selected oligonucleotides.
Figure 8:
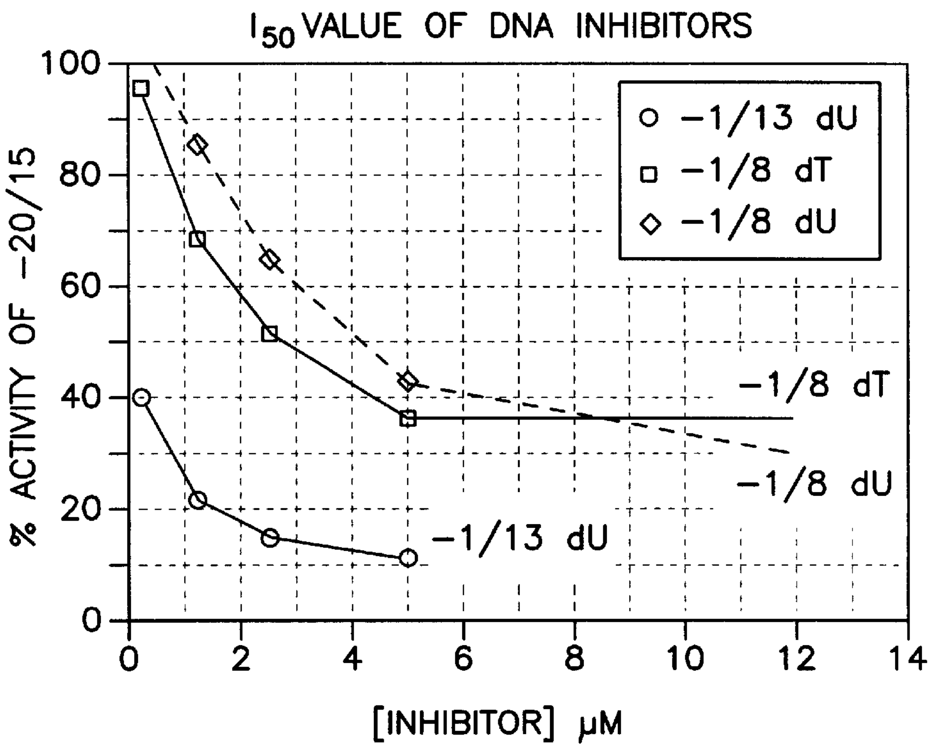
FIG. 8. Graph of $I_{50}$ values of DNA inhibitors. The reaction mixture contained 25 nM of the −20/15 WT template RNA with 10 $\mu$l BMV RdRp in a 40 $\mu$l volume containing 20 mM sodium glutamate (pH 8.2), 4 mM $MgCl_2$, 12.5 mM DTT, 0.5% (vol/vol) Triton X-100, 2 mM $MnCl_2$, 200 $\mu$M ATP and UTP, 500 $\mu$M GTP, and 250 nM [$\alpha$-$^{32}$P]CTP. RdRp products from reactions containing DNA inhibitors (present at 10, 50, 100, 200 and 500-fold molar excess) were quantified and their relative activities were plotted against the amount of inhibitor present. $I_{50}$ values were determined by calculating the amount of inhibitor need to reduce synthesis by 50% of the control reaction.

Termination of RNA-dependent RNA synthesis has not previously been analyzed. The ability of RdRp to synthesize subgenomic or (−)-strand RNA from templates that contain extensions at their 5' ends was tested to determine whether synthesis is programmed to stop at the natural 5' end of the template due to an existing sequence/structure in the template or a natural predilection of RdRp. A subgenomic RNA 250 nt longer than the authentic subgenomic RNA was synthesized by RdRp from a (−)-strand RNA3 template with a 250 nt extension at the 5' end (FIG. 6A; FIG. 6B; lane 3). The 250 nt extension was derived from the Bluescript II KS(+) plasmid (Stratagene) containing the BMV RNA3 cDNA. Although a faint product is visible at the location of the authentic subgenomic RNA from the reaction containing the template with the 5' extension, it is also visible in the lane containing products from a reaction to which no template was added indicating that it is due to endogenous template in the RdRp preparation (FIG. 6B, lanes 3 and 4). A similar (+)-strand RNA3 template with a plasmid-derived 150 nt 5' extension was used to examine termination during (−)-strand synthesis (FIG. 6A, FIG. 6C). A (−)-strand product 150 nt longer than the authentic RNA3 was synthesized from the template with a 150 nt 5' extension (FIG. 6C, lane 3). These results demonstrate that the sequences at the authentic 5' ends of the (−)- and (+)-strand templates do not cause the RdRp to terminate RNA synthesis. They further demonstrate that RdRp is not programmed to stop after synthesis of the wild-type length of RNA. In fact, an extension of 2000 nt, generating a 4200 nt template for (−)-strand RNA3 synthesis led to synthesis of a 4200 nt product. These results do not, however, preclude the possibility that the extensions have altered a structure normally present at the 5' end of wild-type templates that signals termination.

Discussion

Subgenomic RNA is currently the only (+)-strand RNA synthesized in vitro by the BMV RdRp. Thus, subgenomic RNA synthesis is a model for analysis of the mechanism of (+)-strand RNA synthesis. Subgenomic RNA synthesis was characterized with respect to sequence requirements for initiation. A mechanistic comparison can now be made between synthesis from the BMV subgenomic and (−)-stand promoters (Table 1), as well as to DNA-dependent RNA synthesis.

TABLE 1

Comparison of subgenomic and genomic (−)-strand synthesis in vitro.

| Characteristic | Similarities | Differences |
|---|---|---|
| Promoter Location | | Subgenomic synthesis initiates internally using a promoter distinct from template while (−)-strand synthesis initiates near end of template using a promoter contained within template |
| Initiation Sequence | Sequences surrounding initiation nucleotide influence synthesis | Subgenomic synthesis has preference for +2 adenylate<br>(+)-strand initiation sequences (subgenomic and genomic) are highly conserved and very different from those for (−)-strand synthesis |
| NTP Requirements | Require high GTP concentration | Subgenomic synthesis requires high UTP concentration |
| Primer Use | Primers used when GTP is limiting | (−)-strand synthesis more efficiently stimulated by primers |
| Abortive Initiation | Precedes elongation | |
| Termination | Sequence-independent | |

Comparison of initiation sequence requirements for BMV subgenomic and (−)-strand RNA synthesis In the context of truncated templates containing the subgenomic promoter, mutational analysis has demonstrated a strong preference for the +1 cytidylate (Adkins et al., 1997; Siegel et al., 1997). Similar analysis has suggested the penultimate cytidylate of genomic RNAs functions as the normal initiation site for (−)-strand synthesis (Dreher et al., 1984; Dreher & Hall, 1988). However, there may be some flexibility in the selection of the initiation site; mutation of the authentic +1 cytidylate in the template for subgenomic RNA synthesis can result in initiation from a cytidylate inserted one nucleotide 3' or 5' of the original initiation site (Siegel et al., 1997). In proscript −1G/A, the 16 nt product likely arises from initiation at the −2 cytidylate, which resembles the authentic initiation site by forming a cytidylate-adenylate pair. In proscript −1G/U, the 15 nt product likely arises from inefficient RdRp initiation from the −1 uridylate using an adenylate, as previously observed (Siegel et al., 1997). The observation that incorrectly initiated products are produced at low abundance indicates that the catalytic site of RdRp is positioned and somewhat sterically constrained over the authentic +1 site.

The identity of the −1 nt in the template for subgenomic synthesis does not affect the efficiency of initiation (FIGS. 1A and 1B), whereas previous reports show replacement of the −1 adenylate with a cytidylate or uridylate reduces (−)-strand synthesis to approximately 30% of that from the wild-type sequence (Dreher et al., 1984; Dreher & Hall, 1988; Sun et al., 1996). A preference for a +2 adenylate for subgenomic synthesis was observed (FIGS. 1A and 1B). Although the +2 nt influences (−)-strand synthesis, it can be changed from a cytidylate to a uridylate with only a moderate decrease in synthesis, whereas a cytidylate to adenylate change actually increased synthesis in vitro. The cytidylate to adenylate change makes the context of the (−)-strand initiation site more similar to that of the subgenomic initiation site. Thus, although the +2 nt affects both subgenomic and (−)-strand synthesis, all mutations at +2 are detrimental to subgenomic RNA synthesis, whereas they have varying effects on (−)-strand RNA synthesis.

Conservation of Initiation Sequences in the Alphavirus-like Superfamily

Definition of the BMV subgenomic and (−)-strand initiation sequences allows a closer examination of initiation sequences of other members of the alphavirus-like superfamily. The subgenomic initiation sequences of 16 representative alpha-like viruses analyzed adhered to the +1 pyrimidine and +2 adenylate rule (Table 2). Similarly, except for Barmah Forest virus (which has an additional uridylate at the 3' end), the initiation sequences for genomic (+)-strand synthesis also followed the pyrimidine-adenylate rule (Table 2). Although the pyrimidine found at the +1 position varies between viruses, within each virus the same pyrimidine is found at the +1 position for both subgenomic and genomic (+)-strand initiation.

TABLE 2

Comparison of initiation sequences for genomic (+)-strand, subgenomic and genomic (−)- strand RNA synthesis in the alphavirus-like superfamily.

| Virus | RNA | Initiation sequence for synthesis of: genomic (+)-strand | subgenomic | genomic (−)-strand |
|---|---|---|---|---|
| Plant-infecting: | | | | |
| | | +1 | | +1 |
| Brome Mosaic[a] | 1 | 3' CAUC 5' | | 3' ACCAGA 5' |
| | 2 | CAUU | +1 | ACCAGA |
| | 3 | CAAG | 3'CAUA 5' | ACCAGA |
| Cowpea Chlorotic Mottle[a] | 1 | CAUU | | ACCAGA |
| | 2 | CAUU | | ACCAGA |
| | 3 | CAUU | CAUU | ACCAGA |
| Broad Bean Mottle[a] | 1 | UAUU | | ACCAGA |
| | 2 | UAUU | | ACCAGA |
| | 3 | UAUU | UAUU | ACCAGA |
| Cucumber Mosaic (Q, fny)[a] | 1 | CAAA | | ACCAGA |
| | 2 | CAAA | | ACCAGA |
| | 3 | CAUU | CAAA(Q) | ACCAGA |

TABLE 2-continued

Comparison of initiation sequences for genomic (+)-strand, subgenomic and genomic (-)- strand RNA synthesis in the alphavirus-like superfamily.

| | | Initiation sequence for synthesis of: | | |
|---|---|---|---|---|
| Virus | | genomic RNA (+)-strand | subgenomic | genomic (-)-strand |
| Tobacco Mosaic (Vulgare)[b] | | CAUA | CAAU (fny)<br>CAAA (30K)<br>CAAA (CP) | ACCCGG |
| Alfalfa Mosaic[c] | 1 | CAAA | | CGAGGG |
| | 2 | CAAA | | CGAGGG |
| | 3 | CAAA | CAAA | CGAGGG |
| Animal-infecting: | | | | |
| Sindbis[d] | | UACC | UAUC | CUUUAC |
| Semliki Forest[d] | | UACC | UAAC | CCUUUA |
| Aura[e] | | UAUC | UAUC | CUUUAU |
| Barmah Forest[f] | | UUAG | UAUC | CAUUUU |
| Eastern Equine Encephalitis[d] | | UAUC | UAUC | CUUUAU |
| Venezuelan Equine Encephalitis[d] | | UACC | UACC | CUUUAU |
| Middleburg[d] | | UAAC | UAUC | CCUUAU |
| Ockelbo[g] | | UAAC | UAUC | CUUUAC |
| O'Nyong-nyong[h] | | UAUC | UAUC | CUUUAU |
| Ross River[i] | | UACC | UAUC | CAUUUU |

Strains are indicated in parentheses where multiple strains of one virus have been sequenced.
Tobacco mosaic virus produces two subgenomic RNAs: one for the movement protein (30K) and one for the coat protein (CP).
[a]Ahlquist et al., 1981a; [b]Goelet et al., 1982; [c]Gunn & Symons, 1980; [d]Ou et al., 1982a, 1982b, 1983; [e]Rumenapf et al., 1995; [f]Lee et al., 1997; [g]Shirako et al., 1991; [h]Levinson et al., 1990; [i]Faragher & Dalgarno, 1986; Faragher et al., 1988.

The initiation sequences for (−)-strand synthesis in the plant-infecting representatives of the alphavirus-like superfamily are similar to one another except for alfalfa mosaic virus. For the animal-infecting representatives, all of the initiation sequences for (−)-strand synthesis are pyrimidine-rich. Although there is a fairly high degree of conservation in the (−)-strand initiation sequences within the plant- or animal-infecting representatives, these sequences are dissimilar from those for subgenomic or (+)-strand genomic synthesis. The initiation sequences suggest that (+)- and (−)-strand synthesis are fundamentally different, whereas (+)-strand synthesis, subgenomic and genomic, shares common themes in the alphavirus-like family. The initiation pyrimidine and the +2 adenylate may participate in directing accurate/efficient (+)-strand RNA synthesis, as reported recently by Van Rossum et al. (1997) for alfalfa mosaic virus. Siegel et al. (1997) demonstrated that nucleotides within the BMV subgenomic core promoter upstream of the initiation site function in recognition of the template by RdRp and our current data indicates that the +1 and +2 nucleotides are also critical for subgenomic RNA synthesis. These two nucleotides may be contacted by RdRp and/or may be important for directing incorporation of a guanylate and uridylate. The lack of common functional groups in the nucleotides that can serve at the +2 position (adenylate, cytidylate, and uridylate) suggests that the +2 position may be more important for directing incorporation of the appropriate nucleotide.

Comparison of Initiation Requirements for Subgenomic and (−)-strand Synthesis

The initiation complex is formed by the intermolecular interaction of the template, RdRp, and initiation nucleotides. Although initiation generally requires a guanylate, several lines of evidence suggest that the initiation complex may be different for subgenomic and (−)-strand RNA synthesis. We observed that the stimulation of subgenomic synthesis by primers was markedly less than for (−)-strand synthesis. Several possibilities may explain these observations. Template RNA sequence and/or structure may determine priming efficiency. Perhaps a more open structure exists at the promoter for (−)-strand synthesis due to its location near the 3' end of the template RNA or to a different conformation of the RdRp complex for subgenomic and (−)-strand synthesis. Finally, different subunits within RdRp may be required for subgenomic and (−)-strand synthesis.

Primers never restore RNA synthesis by the BMV RdRp to the levels observed with optimal concentrations of GTP. Reactions containing GTP concentrations that allow efficient (−)-strand RNA synthesis were not affected by the addition of GMP, GDP, or GpG, eliminating the possibility that these primers have a significant inhibitory effect on RNA synthesis (data not shown). This suggests that, in addition to the guanylate, one or more of the three phosphates may contribute to recognition by RdRp and is especially relevant for synthesis of the subgenomic RNA. Because the subgenomic and genomic (+)-strand RNAs are capped and capping requires the β and γ phosphates, it is tempting to speculate that the efficient use of GTP as the initiation nucleotide may be linked to capping.

Synthesis of Abortive Products Precedes BMV and RdRp Elongation of Subgenomic and (−)-strand RNAs In contrast to the apparent differences in the initiation of subgenomic and (−)-strand synthesis, the transition from initiation to elongation may occur via a similar mechanism.

Abortive products synthesized during initiation of subgenomic and (−)-strand genomic RNA synthesis are as long as nine nucleotides (FIG. 4) and eight nucleotides (Sun et al., 1996), respectively. Because the longest abortive product is a good indicator for the position of the transition of RdRp to productive synthesis, the transition likely occurs after the synthesis of seven to eight phosphodiester bonds for both subgenomic and (−)-strand RNA synthesis. The stoichiometry of the reactions is also similar in that a 3–20-fold molar excess of the abortive products is synthesized in comparison to full-length products. Finally, low concentrations of manganese had similar stimulatory effects on both subgenomic and (−)-strand abortive product synthesis.

Comparison of RNA-dependent and DNA-dependent RNA Synthesis

RdRps and DdRps have evolved to use different templates. In addition, although both types of polymerases initiate RNA synthesis internally within the template, RdRp must also be able to initiate RNA synthesis near the 3' ends of templates. Recent elucidation of the structures of several polymerases, including the polio-virus RdRp, revealed that the three-dimensional structures of the polymerases are more similar than their primary sequences (Joyce & Steitz, 1995; Hansen et al., 1997; Doublié et al., 1998). After characterization of both subgenomic and (−)-strand RNA synthesis by the BMV RdRp, we find that the structurally similar RdRps and DdRp share many biochemical activities and follow a highly parallel series of steps, including initiation, abortive initiation, transition to elongation, elongation, and termination (Table 3).

TABLE 3

Comparison of RNA synthesis by DdRp and RdRp.

| Characteristic | DdRp | RdRp |
|---|---|---|
| Initiation | Purine[a] | Purine[bcd] |
| | Primer-inducible[e] | Primer-inducible[fgh] |
| | Sequence-specific[i] | Sequence-specific[j] |
| | High Km for initiation nucleotide[k] | High Km for initiation nucleotide[gl] |
| Abortive Initiation | DdRp remains on template[m] | RdRP dissociates from template[n] |
| Template Commitment | 8–12 nts[o] | ca. 10 nts[hp] |
| cis-acting Regulatory | Enhancers[q] | Activator[c] |
| Sequences | Repressors[q] | Repressors[r] |
| Termination | Sequence-dependent[s] | Sequence-independent[h] |

[a]McClure, 1985; [b]Blumenthal, 1980; Miller et al., 1985; Miller et al., 1986; [c]Adkins et al., 1997; [d]Siegel et al., 1997; [e]Terao et al., 1972; Cazenave & Uhlenbeck, 1994; [f]Blumenthal & Carmichael, 1979; Honda et al., 1986; [g]Kao & Sun, 1996; [h]this work; [i]Martin & Coleman, 1987; Milligan et al., 1987; Maslak et al., 1993; Schick & Martin, 1993; [j]Siegel et al., 1997; [k]Patra et al., 1992; [l]Mitsunari & Hori, 1973; [m]Carpousis & Gralla, 1980; [n]Sun et al., 1996; Sun & Kao, 1997a; [o]Levin et al., 1987; [p]Sun & Kao, 1997b; [q]Tjian, 1996; [r]Bujarski et al., 1985; [s]Richardson, 1996.

Initiation of RNA synthesis by both RdRp and DdRp strongly prefers a purine nucleotide, which is used at a higher concentration for initiation than for elongation (Blumenthal, 1980; McClure, 1985; Kao & Sun, 1996). BMV RdRp prefers GTP as the initiation nucleotide, but can use ATP with lower efficiency (FIG. 3) (Siegel et al., 1997). The initiation nucleotide can be considered as a primer because it is not hydrolyzed during the formation of the first phosphodiester bond. Other primers of one or a few nucleotides can substitute for the initiation nucleotide for RdRp (FIG. 3) (Blumenthal & Carmichael, 1979; Honda et al., 1986; Kao & Sun, 1996) and the T7 and *Escherichia coli* DdRps (Terao et al., 1972).

The lengths of the abortive initiation products formed by both DdRp and RdRp are strikingly similar. The maximum lengths of abortive initiation products tend to be 9–12 nt for both the T7 (Martin et al., 1988) and *E. coli* DdRps (Leven et al., 1987), whereas the maximum sizes of abortive products synthesized by RdRps are 8–9 nt (FIG. 4B) (Furuichi, 1981; Yamakawa et al., 1981; Sun et al., 1996; Sun & Kao, 1997b). Finally, the abortive products synthesized by the BMV RdRp and the T7 DdRp tend to occur after the polymerization of an adenylate or uridylate (Martin et al., 1988).

Several lines of evidence suggest that abortive initiation plays significant roles in vivo and in vitro. It is likely that abortive initiation allows the dissociation of polymerase from inappropriate templates because abortive synthesis by the T7 DdRp can occur on random DNA polymers, but the polymerase does not switch to the elongation mode (Sousa et al., 1992). In addition, the abortive products may act as primers to increase the transition rate of polymerase into the elongation phase. Ruetsch and Dennis (1987) observed that in the presence of primers, the transition from an initiation to a salt-resistant elongation stage occurred after synthesis of the third phosphodiester bond. Finally, Nagy et al. (1997) provided evidence for the use of abortive initiation products in repairing small deletions in the 3' ends of turnip crinkle virus RNAs. This is a plausible mechanism for repair of the ends of genomic segments of multipartite RNA viruses and may explain the telomerase-like activity proposed to be responsible for maintenance of BMV RNA 3' ends (Rao et al., 1989).

In summary, the brome mosaic virus (BMV) RNA-dependent RNA polymerase (RdRp) directs template-specific synthesis of (−)-strand genomic and (+)-strand subgenomic RNAs in vitro. While the requirements of (−)-strand RNA synthesis have been previously characterized, the mechanism of subgenomic RNA synthesis has not. Mutational analysis of the subgenomic promoter revealed that the +1 cytidylate and the +2 adenylate are important for RNA synthesis. Phylogenetic analysis of the sequences surrounding the initiation sites for subgenomic and genomic (+)-strand RNA synthesis in all members of the alphavirus-like superfamily revealed that the +1 and +2 positions are highly conserved as a pyrimidine-adenylate.

Example 3

Figure 9A:
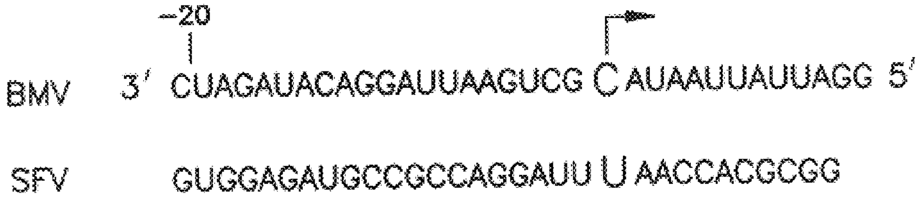
FIG. 9. (A) Sequences from BMV (SEQ ID NO:1) and SFV (SEQ ID NO:11) used to test RNA synthesis by the BMV RNA-dependent RNA polymerase in vitro. The arrow denotes the position of the initiation nucleotide.
Figure 9B:
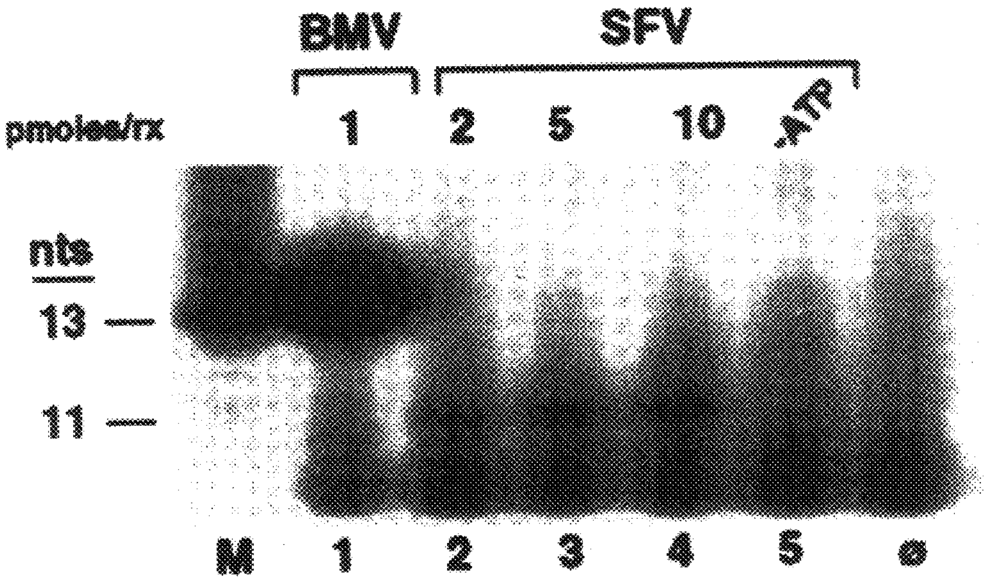

FIG. 9 shows that the BMV RdRp can utilize the promoter from an animal RNA virus, Semliki Forest virus (SFV), and initiate RNA synthesis from the nucleotide used by the SFV polymerase in vivo (lanes 2–4). This demonstrates that the initiation is specific since a reaction lacking the initiation nucleotide ATP did not result in synthesis of the 11 nt product (lane 5).

Example 4

To determine whether short RNAs corresponding to the initiation sequence can inhibit RNA synthesis, an in vitro assay was employed (Table 5). The reaction was performed with a tester template and increasing concentrations of the competitor RNA. The results were then plotted as the percentage of activity of the tester template in the presence of increasing concentrations of inhibitors. This plot yielded the inhibitor concentration needed to reduce synthesis by 50% ($I_{50}$).

TABLE 5

Effect of various RNAs and DNA competitors on RNA synthesis by RdRp

| Competitor | Name | $I_{50}$ (nM) |
|---|---|---|
| RNA | −20/13 + 1 c/g | 125 |
| | −20/5 + 1 c/g | 95 |
| | −20/3 + 1 c/g | 80 |
| | −20/−1 | >>250 |
| DNA | −1/13 | 125 |
| | −1/8 | 2500 |

A competitor RNA of 33 nts (wt-13) which contained the wild-type promoter and initiation sequence reduced the synthesis from the tester template (wt-15). The concentration for the wt-13 RNA needed to reduce wt-15 synthesis to 50% ($I_{50}$) was 20 nM. To determine the length required for efficient inhibition of RNA synthesis from the tester template, an RNA of 23 nt containing the promoter and an additional three nucleotides was employed. This RNA had an $I_{50}$ of 80 nM. The control, an RNA which did not contain an initiation nucleotide (−20/−1), had an $I_{50}$ much greater than 250 nM. Moreover, no significant inhibition was observed with this template even when it was present at 250 nM. These results suggest that relatively low concentrations of short RNAs are potent inhibitors of RNA synthesis by the viral RdRp. An 8 nt competitor DNA molecule containing the initiation nucleotide, but lacking the promoter sequence, also competed for synthesis from the tester template. This 8 nt DNA has an $I_{50}$ of 2.5 micromolar. This result also indicates that single stranded DNA can be used to inhibit viral replication, an observation that is of interest for pharmaceuticals, given the inherently increased stability of DNA molecules in human serum.

REFERENCES

Adkins, S., Siegel, R. W., Sun J. H., Kao C. C. 1997. Minimal templates directing accurate initiation of subgenomic RNA synthesis in vitro by the brome mosaic virus RNA-dependent RNA polymerase. *RNA,* 3, 634–647.

Ahlquist, P. 1992. Bromovirus RNA replication and transcription. *Curr. Opin. Genet. Dev.,* 2, 71–76.

Ahlquist. P., Bujarski J. J., Kaesberg, P., Hall T. C. 1984. Localization of the replicase recognition site within brome mosaic virus RNA by hybrid-arrested RNA synthesis. *Plant Mol. Biol.,* 3, 37–44.

Ahlquist, P., Dasgupta, R., Kaesberg, P. 1981a. Near identity of 3' RNA secondary structure in bromo viruses and cucumber mosaic virus. *Cell,* 23, 183–189.

Ahlquist, P., Luckow, V., Kaesberg, P. 1981b. Complete nucleotide sequence of brome mosaic virus RNA3. *J. Mol. Biol.,* 153, 23–38.

Blumenthal, T. 1980. Qβ replicase template specificity: Different templates require different GTP concentrations for initiation. *Proc. Natl. Acad. Sci. USA,* 77, 2601–2605.

Blumenthal, T., Carmichael, G. G. 1979. RNA replication: function and structure of Qβ replicase. *Annu. Rev. Biochem.,* 48, 525–548.

Bujarski, J. J., Dreher, T. W., Hall, T. C. 1985. Deletions in the 3'-terminal tRNA-like structure of brome mosaic virus RNA differentially affect aminoacylation and replication in vitro. *Proc. Natl. Acad. Sci. USA,* 82, 5636–5640.

Carpousis, A. J., Gralla, J. 1980. Cycling of ribonucleic acid polymerase to produce oligonucleotides during initiation in vitro at the lacUV5 promoter. *Biochemistry,* 19, 3245–3253.

Carpousis, A. J., Gralla, J. 1985. Interaction of RNA polymerase with LacUV5 promoter DNA during mRNA initiation and elongation: Footprinting, methylation and rifampicin-sensitivity changes accompanying transcription initiation. *J. Mol. Biol.,* 183, 165–177.

Cazenave, C., Uhlenbeck, O. C. 1994. RNA template-directed RNA synthesis by T7 RNA polymerase. *Proc. Natl. Acad. Sci. USA,* 91, 6972–6976.

Dasgupta, R., Kaesberg, P. 1982. Complete nucleotide sequences of the coat protein messenger RNAs of brome mosaic virus and cowpea chlorotic mottle virus. *Nucleic Acids Res.,* 1, 703–713.

Dreher, T. W., Hall, T. C. 1988. Mutational analysis of the sequence and structural requirements in brome mosaic virus RNA for minus strand promoter activity. *J. Mol. Biol.,* 201, 31–40.

Dreher, T. W., Bujarski, J. J., Hall, T. C. 1984. Mutant viral RNAs synthesized in vitro show altered aminoacylation and replicase template activities. *Nature* (London) 311, 171–175.

Faragher, S. G., Dalgarno, L. 1986. Regions of conservation and divergence in the 3' untranslated sequences of genomic RNA from Ross River virus isolates. *J. Mol. Biol.,* 190, 141–148.

Faragher, S. G., Meek, A. D. J., Rice, C. M., Dalgarno, L. 1988. Genome sequences of a mouse-avirulent and mouse-virulent strain of Ross River virus. *Virology,* 163, 509–526.

French, R., Ahlquist, P. 1988. Characterization and engineering of sequences controlling in vivo synthesis of brome mosaic virus subgenomic RNA. *J. Virol.,* 62, 2411–2420.

Furuichi, Y. 1981. Allosteric stimulatory effects of S-adenosylmethionine on the RNA polymerase in cytoplasmic polyhedrosis virus. *J. Biol. Chem.,* 256, 483–493.

Goldbach, R., LeGall, O., Wellink, J. 1991. Alpha-like viruses in plants. *Semin. Virol,* 2, 19–25.

Goelet, P., Lomonosoff, G. P., Butler, P. J. G., Akam, M. E., Gait, M. J., Karn, J. 1982. Nucleotide sequence of tobacco mosaic virus. *Proc. Natl. Acad. Sci. USA,* 79, 5818–5822.

Gunn, M. R., Symons, R. H. 1980. Sequence homology at the 3'-termini of the four RNAs of the alfalfa mosaic virus. *FEBS Letters,* 109, 145–150.

Hansen, J. L., Long, A. M., Schultz, S. C. 1997. Structure of the RNA-dependent RNA polymerase of poliovirus. *Structure* (London) 5, 1109–1122.

Hardy, S. F., German, T. L., Loesch-Fries, L. S., Hall, T. C. 1979. Highly active template-specific RNA-dependent RNA polymerase from barley leaves infected with brome mosaic virus. *Proc. Natl. Acad. Sci. USA,* 76, 4956–4960.

Honda, A., Mizumoto, K., Ishihama, A. 1986. RNA polymerase of influenza virus: Dinucleotide-primed initiation of transcription at specific positions on viral RNA. *J. Biol. Chem.,* 261, 5987–5991.

Janda, M., French, R., Ahlquist, P. 1987. High efficiency T7 polymerase synthesis of infectious RNA from cloned brome mosaic virus cDNA and effects of 5' extensions on transcript infectivity. *Virology,* 158, 259–262.

Joyce, C. M., Steitz, T. A. 1995. Polymerase structures and function: Variations on a Theme? *J. Lacteriol.,* 177, 6321–6329.

Kao, C. C., Sun, J. H. 1996. Initiation of minus-strand RNA synthesis by the brome mosaic virus RNA-dependent RNA polymerase: Use of oligoribonucleotide primers. J. Virol., 70, 6826–6830.

Lee, E., Stocks, C., Labigs, P., Hislop, A., Straub, J., Marshall, I., Weir, R., Dalgamo, L. 1997. Nucleotide sequence of the barmah forest virus genome. *Virology,* 227,509–514.

Levin, J. R., Krummel, B., Chamberlin, M. J. 1987. Isolation and properties of transcribing ternary complexes of *Escherichia coli* RNA polymerase positioned at a single template base. *J. Mol. Biol.,* 196, 85–100.

Levinson, R., Strauss, J. H., Strauss, E. G. 1990. Determination of the complete nucleotide sequence of the genomic RNA of O'Nyong-nyong virus and its use in the construction of phylogenetic trees. *Virology,* 175, 110–123.

Marsh, L. E., Dreher, T. W., Hall, T. C. 1988. Mutational analysis of the core and modulator sequences of the BMV RNA3 subgenomic promoter. *Nucleic Acids Res.,* 16, 981–995.

Martin, C. T., Coleman, J. E. 1987. Kinetic analysis of T7 RNA polymerase-promoter interactions with small synthetic promoters. Biochemistry, 26, 2690–2696.

Martin, C. T., Muller, D. K., Coleman, J. E. 1988. Processivity in early stages of transcription by T7 RNA polymerase. *Biochemistry,* 27, 3966–3974.

Maslak, M., Jaworski, M. D., Martin, C. T. 1993. Tests of a model for promoter recognition by T7 RNA polymerase: Thymine methyl group contacts. *Biochemistry,* 32, 4270–4274.

McClure, W. R. 1985. Mechanism and control of transcription initiation in prokaryotes. *Annu. Rev. Biochem.,* 54, 171–204.

Miller, W. A., Hall, T. C. 1983. Use of micrococcal nuclease in the purification of highly template dependent RNA-dependent RNA polymerase from brome mosaic virus-infected barley. *Virology,* 125, 236–241.

Miller, W. A., Dreher, T. W., Hall, T.C. 1985. Synthesis of brome mosaic virus subgenomic RNA in vitro by internal initiation on (–)-sense genomic RNA. *Nature* (London), 313, 68–70.

Miller, W. A., Bujarski, J. J., Dreher, T. W., Hall, T. C. 1986. Minus-strand initiation by brome mosaic virus replicase within the 3' tRNA-like structure of native and modified RNA templates. *J. Mol. Biol.,* 187, 537–546.

Milligan, J. F., Groebe, D. R., Witherell, G. W., Uhlenbeck, 0. C. 1987. Oligoribonucleotide synthesis using T7 RNA polymerase and synthetic DNA templates. *Nucleic Acids Res.,* 15, 8783–8798.

Mitsunari, Y., Hori, K. 1973. Qβ replicase associated poly-cytidylic acid dependent polyguanylic acid polymerase. *J. Biochem.,* 14, 263–271.

Nagy, P. D., Carpenter, C. D., Simon, A. E. 1997. A novel 3'-end repair mechanism in an RNA virus. *Proc. Natl. Acad. Sci. USA,* 94, 1113–1118.

Ou, J—H, Rice, C. M., Dalgamo, L., Strauss, E. G., Strauss, J. H. 1982a. Sequence studies of several alphavirus genomic RNAs in the region containing the start of the subgenomic RNA. *Proc. Natl. Acad. Sci. USA,* 79, 5235–5239.

Ou, J-H, Strauss, E. G., Strauss, J. H. 1983. The 5'-terminal sequences of the genomic RNAs of several alphaviruses. *J. Mol. Biol.,* 168, 1–15.

Ou, J-H, Trent, D. W., Strauss, J. H. 1982b. The 3'-non-coding regions of alphavirus RNAs contain repeating sequences. *J. Mol. Biol.,* 156, 719–730.

Patra, D., Lafer, E. M., Sousa, R. 1992. Isolation and characterization of mutant bacteriophage T7 RNA polymerases. *J. Mol. Biol.,* 224, 307–318.

Quadt, R., Kao, C. Hershberger, R., Browning, K., and Ahlquist, P. 1993. Characterization of a host protein associated with the brome mosaic virus RNA-dependent RNA polymerase. *Proc. Natl. Acad. Sci. USA,* 90, 1498–1502.

Quadt, R., Jaspars, E. M. J. 1990. Purification and characterization of brome mosaic virus RNA-dependent RNA polymerase. *Virology,* 178, 189–194.

Rao, A. L. N., Dreher, T. W., Marsh, L. E., Hall, T. C. 1989. Telomeric function of the transfer RNA-like structure of brome mosaic virus RNA. *Proc. Natl. Acad. Sci. USA,* 86, 5335–5339.

Restrepo-Hartwig, M., Ahlquist, P. 1996. Brome mosaic virus helicase- and polymerase-like proteins colocalize on the endoplasmic reticulum at sites of viral RNA synthesis. *J. Virol,* 70, 8908–8916.

Richardson, J. P. 1996. Structural organization of transcription termination factor Rho. *J. Biol. Chem.,* 271, 1251–1254.

Ruetsch, N., Dennis, D. 1987. RNA polymerase: Limit cognate primer for initiation and stable ternary complex formation. *J. Biol. Chem.,* 262, 1674–1679.

Rumenapf, T., Strauss, E. G., Strauss, J. H. 1995. Aura virus is a new world representative of Sindbis-like viruses. *Virology,* 208, 621–633.

Sambrook, J., Fritsch, E. F, Maniatis T. 1989. *Molecular cloning: a laboratory manual.* Cold Spring Harbor, N.Y.: Cold Spring Harbor Laboratory Press.

Schick, C., Martin, C. T. 1993. Identification of specific contacts in T3 RNA polymerase-promoter interactions: Kinetic analysis using small synthetic promoters. *Biochemistry,* 2, 4275–4280.

Shirako, Y., Niklasson, B., Dalrymple, J. M., Strauss, E. G., Strauss, J. H. 1991. Structure of the Ockelbo virus genome and its relationship to other Sindbis viruses. *Virology,* 182, 753–764.

Siegel, R. W., Adkins, S., Kao, C. C. 1997. Sequence-specific recognition of a subgenomic promoter by a viral RNA polymerase. *Proc. Natl. Acad. Sci. USA,* 94, 11238–11243.

Sousa, R., Patra, D., Lafer, E. M. 1992. Model for the mechanism of bacteriophage T7 RNAP transcription initiation and termination. *J. Mol. Biol.,* 224, 319–334.

Sun, J. H., Kao, C. C. 1997a. RNA synthesis by the brome mosaic virus RNA-dependent RNA polymerase: Transition from initiation to elongation. *Virology,* 233, 63–73.

Sun, J. H., Kao, C. C. 1997b. Characterization of RNA products associated with or aborted by a viral RNA-dependent RNA polymerase. *Virology,* 236, 348–353.

Sun, J. H., Adkins, S., Faurote, G., Kao, C. C. 1996. Initiation of (–)-strand RNA synthesis catalyzed by the BMV RNA-dependent RNA polymerase: Synthesis of oligonucleotides. *Virology,* 226, 1–12.

Terao, T., Dahlberg, J. E., Khorana, H. G. 1972. Studies on polynucleotides. *J. Biol, Chem.,* 247, 6157–6166.

Tijan, R. 1996. The biochemistry of transcription in eukaryotes: A paradigm for multisubunit regulatory complexes. *Phil. Trans. R Soc. London B,* 351, 491–499.

Van Rossum, C. M. A., Neeleman, L., Bol, J. F. 1997. Comparison of the role of 5' terminal sequences of alfalfa mosaic virus RNAs 1, 2, and 3 in viral RNA replication. *Virology,* 235, 333–341.

Yamakawa, M., Furuichi, Y., Nakashima, K., LaFiandra, A. J., Shatkin, A. J. 1981. Excess synthesis of viral mRNA 5'-terminal oligonucleotides by reovirus transcriptase. *J. Biol. Chem.,* 256, 6507–6514.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An in vitro method to identify an oligonucleotide which inhibits a viral polymerase, comprising: contacting at least one oligonucleotide of at least four nucleotides with a mixture which comprises an isolated RNA dependent RNA polymerase of a (+) sense signal stranded RNA virus of the alpha virus family and a nucleic acid template for the polymerase under conditions effective for nucleic acid synthesis by the polymerase, wherein the oligonucleotide comprises a viral nucleic acid sequence which includes a nucleotide required for the initiation of viral nucleic acid synthesis by a RNA dependent RNA polymerase of a (+) sense single stranded RNA virus of the alpha virus family and includes a nucleotide corresponding to a nucleotide in the viral nucleic acid sequence which is 5' to the nucleotide required for initiation; and detecting or determining whether the oligonucleotide inhibits nucleic acid synthesis by the polymerase.

2. The method of claim 1, wherein the oligonucleotide is less than about 50 nucleotides.

3. The method of claim 2 wherein the oligonucleotide includes the contiguous two nucleotides 3' of the nucleotide required for the initiation of viral nucleic acid synthesis.

4. The method of claim 1 wherein the template is subgenomic viral RNA.

5. The method of claim 1 wherein the oligonucleotide is DNA.

6. The method of claim 1 wherein the oligonucleotide is RNA.

7. The method of claim 1 wherein the oligonucleotide is at least about eight nucleotides in length.

8. The method of claim 1 wherein the oligonucleotide is at least about fourteen nucleotides in length.

9. The method of claim 1 wherein the sequence of the oligonucleotide is identical to the sequence of the template.

10. The method of claim 1 wherein the oligonucleotide comprises ribonucleotides and deoxyribonucleotides.

11. The method of claim 1 wherein the oligonucleotide includes a nucleotide analog.

12. The method of claim 11 wherein the nucleotide analog is 2-aminopurine.

13. The method of claim 11 wherein the nucleotide analog is pyrimidine-2-ono- riboside.

14. The method of claim 1 wherein the oligonucleotide includes a nucleotide which is 3' to the nucleotide required for the initiation of viral nucleic acid synthesis.

15. The method of claim 14 wherein the oligonucleotide includes a nucleotide that is an analog of a wild-type nucleotide.

16. The method of claim 14 wherein the nucleotide that is 3' is a purine riboside.

17. The method of claim 10 wherein the oligonucleotide comprises 5' tacG3' or 5'tagG3', wherein t, a, c and g are each a ribonucleotide and G is a deoxyribonucleotide.

18. The method of claim 1 wherein the oligonucleotide comprises a viral nucleic acid sequence from a virus selected from the group consisting of Brome Mosaic Virus, Cowpea Chlorotic Mottle Virus, Broad Bean Mottle Virus, Cucumber Mosaic Virus, Tobacco Mosaic Virus, Alfalfa Mosaic Virus, Sindbis Virus, Semliki Forest Virus, Aura Virus, Barma Forest Virus, Eastern Equine Encephalitis Virus, Venezuelan Equine Encephalitis Virus, Middleburg Virus, Ockelbo Virus, O'Nyong-Nyong Virus and Ross River Virus.

* * * * *